(12) United States Patent
Castro et al.

(10) Patent No.: US 7,842,815 B2
(45) Date of Patent: *Nov. 30, 2010

(54) COMPOUNDS AND METHODS FOR INHIBITING THE INTERACTION OF BCL PROTEINS WITH BINDING PARTNERS

(75) Inventors: Alfredo C. Castro, Winchester, MA (US); Edward B. Holson, Newton Highlands, MA (US); Brian T. Hopkins, Brookline, MA (US); Nii O. Koney, Brighton, MA (US); Daniel A. Snyder, Cambridge, MA (US); Thomas T. Tibbitts, Westford, MA (US)

(73) Assignee: Infinity Pharmaceuticals, Inc., Cambridge, MA (US)

( * ) Notice: Subject to any disclaimer, the term of this patent is extended or adjusted under 35 U.S.C. 154(b) by 859 days.

This patent is subject to a terminal disclaimer.

(21) Appl. No.: 11/600,332

(22) Filed: Nov. 15, 2006

(65) Prior Publication Data

US 2007/0161690 A1 Jul. 12, 2007
US 2008/0306127 A9 Dec. 11, 2008

Related U.S. Application Data

(63) Continuation-in-part of application No. 11/156,364, filed on Jun. 17, 2005.

(60) Provisional application No. 60/580,616, filed on Jun. 17, 2004, provisional application No. 60/659,301, filed on Mar. 7, 2005.

(51) Int. Cl.
   *C07D 261/02* (2006.01)
(52) U.S. Cl. .................................................. 548/240
(58) Field of Classification Search .................. 548/240
   See application file for complete search history.

(56) References Cited

U.S. PATENT DOCUMENTS

| 5,294,617 | A | 3/1994 | Venkatesan et al. |
| 5,514,505 | A | 5/1996 | Limburg et al. |
| 6,221,865 | B1 | 4/2001 | Sebti et al. |
| 6,747,050 | B1 | 6/2004 | Kim et al. |

FOREIGN PATENT DOCUMENTS

| DE | 3643012 A1 | 6/1988 |
| EP | 0769296 A1 | 4/1997 |
| EP | 0970950 A2 | 1/2000 |
| JP | 11343285 A | 12/1999 |
| WO | WO-95/24398 A1 | 9/1995 |
| WO | WO 98/06694 | 2/1998 |
| WO | WO 98/16830 | 4/1998 |
| WO | WO 01/16115 A1 | 3/2001 |
| WO | WO-02/097053 | 12/2002 |
| WO | WO 03/105788 A1 | 2/2003 |
| WO | WO-2006/009869 | 1/2006 |

OTHER PUBLICATIONS

Akmanova, N. A. et al., "Dipolar Addition to Carbamoyl Nitrones", *Zhurnal Organicheskoi Khimii*, 15(10):2061-2065 (Oct. 1979) (English translation).
Baell, J. et al., "Prospects for targeting the Bcl-2 family of proteins to develope novel cytotoxic drugs", *Biochem. Pharmacol.*, 64:851-863 (2002).
Banerji, A. et a., "1,3-Dipolar cycloadditions: Part VII—Cycloaddition of C,N-diarylnitrones to ethyl crotonate", Ind. Journ. of Chem., 43B:1925-1933 (Sep. 2004).
Ding, X. et al., "Catalytic Asymmetric 1,3-Dipolar Cycloaddition of a Nitrone Bearing a Bulky Amide Moiety to γ-Substituted Allylic Alcohols", *Chemistry Letters*, 2002:302-303 (2002).
Dugovic, B., et al., "Reversal of Regioselectivity of Nitrone Cycloadditions by Lewis Acids", Helvetica Chimica Acta, 88:1432-1443 (2005).
Foley, M., "Infinity Pharmaceuticals—Infiniplex Libraries: Developing a Platform for Chemical Genetic Studies", PowerPoint Presentation Oct. 2, 2006.
Foley, M., "Infinity Pharmaceuticals—Chemical Genomics-Linking the Genome to Therapies", PowerPoint Presentation Jun. 11, 2002.
Foley, M., "Infinity Pharmaceuticals—ACS Short Course on Drug Discovery in the 21st Century—Arrayed Split-Pool Libraries: Developing a Platform for Chemical Genetic Studies", PowerPoint Presentation Jul. 10, 2002.
"Infinity Pharmaceuticals—ACS Prospectives Conference Series", PowerPoint Presentation Sep. 22, 2003.
"Infinity Pharmaceuticals—Cambridge Health Institute's Conference on Diversity-Oriented Synthesis (DOS) and Natural Product Chemistry", PowerPoint Presentation Oct. 9, 2003.
Inouye, Y., et al., "Regioselective Effects of the Allylic Heteroatoms in 1,3-Dipolar Cycloaddition of Nitrones to Several Allyl Derivatives", Heterocycles, 25:109-111 (1987).
Jen, W. S., et al., "New Strategies for Organic Catalysis: The First Enantioselective Organocatalytic 1,3-Dipolar Cycloaddition", J. Am. Chem. Soc., 122:9874-9875 (2000).
Kanemasa, S. et al., "Metal Ion-Mediated Diastereoface-Selective Nitrone Cycloadditions. Reaction Mechanism for the Reversal of Regioselectivity Observed in the Magnesium and Zinc Ion-Mediated Nitrone Cycloadditions of Allylic Alcohols", Tetrahedron Letters, 36(28):5019-5022 (1995).
Kanemasa, S. et al., "Metallic Base-Induced and Lewis Acid-Catalyzed Nitrone Cycloadditions to Allyl Alcohol Dipolarophiles. Highly Effective Regio- and Stereocontrol", Tetrahedron Letters, 34(1):87-90 (1993).
Kano, T. et al., "Asymmetric 1,3-Dipolar Cycloaddition Reaction of Nitrones and Acrolein with a Bis-Titanium Catalyst as Chiral Lewis Acid", J. Am. Chem. Soc., 127:11926-11927 (2005).
Merino, P. et al., "1,3-Dipolar Cycloadditions of N-Benzyl Furfuryl Nitrones with Electron-rich Alkenes", Molecules, 5:132-152 (2000).

(Continued)

*Primary Examiner*—Robert Havlin
(74) *Attorney, Agent, or Firm*—Foley Hoag LLP

(57) ABSTRACT

One aspect of the present invention relates to heterocyclic compounds that bind to bcl proteins and inhibit Bcl function. Another aspect of the present invention relates to compositions comprising a heterocyclic compound of the invention. The present invention provides methods for treating and modulating disorders associated with hyperproliferation, such as cancer.

3 Claims, No Drawings

OTHER PUBLICATIONS

Merino, P. et al., "A DFT Study on the 1,3-Dipolar Cycloaddition Reactions of C-(methylcarbonyl)-N-methyl nitrone with methyl acrylate and vinyl acetate", Tetrahedron, 59:3581-3592 (2003).

Niu, D. et al., "Non-Cycloaddition Approach to Regioselective Synthesis of Isoxazolidines", Synlett, 979-980 (Sep. 1998).

Puglisi, A. et al., "Enantioselective 1,3-Dipolar Cycloadditions of Unsaturated Aldehydes Promoted by a Poly(ethylene glycol)-Supported Organic Catalyst", Eur. J. Org. Chem., 567-573 (2004).

Ratts, K. W. et al., "Chemistry of Resonance-Stabilized Sulfonium Ylids", *Journal of Organic Chemistry*, 31(6):1689-1693 (1966).

Ratts, K. W. et al., "Chemistry of Resonance-Stabilized Sulfonium Ylids", J. Org. Chem., 1689-1693 (Jun. 1966).

Revuelta, J. et al., "Samarium(II) iodide reduction of isoxazolidines", Tetrahedron Letters, 45:8375-8377 (2004).

Saito, T. et al., "Evaluation of chiral bidentate ligand-metal complexes in asymmetric 1,3 dipolar cycloaddition reaction of nitrones with 3-alkenoyl-2-oxazolidinones", Tetrahedron Letters, 45:9581-9584 (2004).

Sibi, M. P. et al., "Exo Selective Enantioselective Nitrone Cycloadditions", J. Am. Chem. Soc., 126:718-719 (2004).

Tan, D. S. et al., "Stereoselective Synthesis of over Two Million Compounds Having Structural Features Both Reminiscent of Natural Products and Compatible with Miniaturized Cell-Based Assays", *J. Am. Chem. Soc.*, 12:08565-8566 (1998).

Byrn et al., "Pharmaceutical Solids: A Strategic Approach to Regulatory Considerations," Pharmaceutical Research, 12(7):945-954 (1995).

Kubinyi (3D QSAR in Drug Design: Ligand-Protein Interactions and Molecular Similarity, Vo. 2-3, Springer, 800 pages (1998).

Blanáriková-Hlobilová, I. et al., "Steroselectivity of 1,3-dipolar cycloadditions of L-vatine-derived nitrones with methyl acrylate," Tetrahedron 59, 3333-3339 (2003).

COMPOUNDS AND METHODS FOR INHIBITING THE INTERACTION OF BCL PROTEINS WITH BINDING PARTNERS

RELATED APPLICATIONS

This application is a continuation-in-part of U.S. patent application Ser. No. 11/156,364, filed Jun. 17, 2005; which claims the benefit of priority to U.S. Provisional patent application Ser. Nos. 60/580,616, filed Jun. 17, 2004; and 60/659,301, filed Mar. 7, 2005.

FIELD OF THE INVENTION

The invention is in the field of cancer therapeutics. Specifically, the present invention is in the field of cancer therapeutics that promote apoptosis in tumor cells using isoxazolidine analogs. The isoxazolidine compounds of the invention bind to Bcl proteins and block Bcl anti-apoptotic function in cancer cells and tumor tissue expressing the Bcl proteins. The compounds, and pharmaceutical compositions comprising these compounds, may be used in the treatment of cancerous disease either alone or in combination with chemotherapeutics or other drugs.

BACKGROUND OF THE INVENTION

Apoptosis, or programmed cell death, is important for normal embryological/ananatomical development, host defense and suppression of oncogenesis. Faulty regulation of apoptosis has been implicated in cancer and many other human diseases which result from an imbalance between the process of cell division and cell death. Bcl-2 was originally identified at the chromosomal breakpoint of t(14;18)-bearing B-cell lymphomas and belongs to a growing family of proteins which regulate apoptosis. (Gross, A; McDonnell, J M; Korsmeyer, S. J. BCL-2 family members and the mitochondria in apoptosis. Genes & Development 1999, 13, 1899-1911, Cory, S.; Huang, D. C. S.; Adams, J. M. The Bcl-2 family: roles in cell survival and oncogenesis. Oncogene, 2003 22, 8590-8607. Danial, N. N.; Korsmeyer, S. J. Cell death: Critical control points. Cell 2004, 116, 205-218. Chao, D. T.; Korsmeyer, S. J. Bcl-2 family: regulators of cell death. Annu. Rev. Immunol. 1998, 16, 395-419). Apoptosis, Christopher Potten, James Wilson, Cambridge University Press, 2004). The Bcl-2 family of proteins include both anti-apoptotic molecules, such as Bcl-2 and Bcl-XL, and pro-apoptotic molecules, such as Bax, Bak, Bid and Bad. Bcl-2 contributes to cancer cell progression by preventing normal cell turnover caused by physiological cell-death mechanisms. Over-expression of Bcl-2 has been observed in 70% of breast cancer and many other forms of cancer (Buolaniwini, J. K. Novel anticancer drug discovery. Curr. Opin. Chem. Biol. 1999, 3, 500-509). The expression levels of Bcl-2 proteins also correlate with resistance to a wide spectrum of chemotherapeutic drugs and γ-radiation therapy (Reed, J. C.; Miyashita, T.; Takayama, S.; Wang, H.-G.; Sato, T.; Krajewski, S.; Aime-Sempe, C.; Bodrug, S.; Kitada, S.; Hanada, M. Bcl-2 family proteins: Regulators of cell-death involved in the pathogenesis of cancer and resistance to therapy. J. Cell. Biochem. 1996, 60, 23-32; Reed, J. C. Bcl-2 family proteins: strategies for overcoming chemoresistance in cancer. Advances in Pharmocology 1997, 41, 501-553; Strasser, A.; Huang, D. C. S.; Vaux, D. L. The role of the Bcl-2/ced-9 gene family in cancer and general implications of defects in cell death control for tumorigenesis and resistance to chemotherapy. Biochem. Biophys. Acta 1997,1333, F151-F189; DiPaola, R. S.; Aisner, J. Overcoming Bcl-2- and p53-mediated resistance in prostate cancer. Semin. Oncol. 1999, 26, 112-116).

Members of the Bcl-2 family of proteins represent key regulators of apoptosis, with pro-apoptotic (e.g., Bax, Bak, Bid, Bim, Noxa, Puma) and anti-apoptotic function (e.g., Bcl-2, Bcl-xL, Mcl-1). Selective and competitive dimerization between pro- and anti-apoptotic members of the family determines the fate of a cell given pro-apoptotic stimulus. Although the precise roles of Bcl-2 and Bcl-xL in cancer are not completely understood, there are several lines of evidence that suggest that Bcl-2 and Bcl-xL not only contribute to cancer progression by preventing normal cell turnover, but also play a role in the resistance of cancer cells to current cancer treatments. Experimental over-expression of Bcl-2 (Bcl-xL) renders cancer cells resistant to a wide spectrum of chemotherapeutic agents and radiation (Bcl-2 family proteins: Regulators of cell-death involved in the pathogenesis of cancer and resistance to therapy. J. Cell. Biochem. 1996, 60, 23-32; Reed, J. C). Bcl-2 and/or Bcl-xL are over-expressed in more than 50% of all tumors as shown below (from Wang, S.; Yang, D.; Lippman, M. E. Targeting Bcl-2 and Bcl-xL with nonpeptidic small-molecule antagonists. Seminars in Oncology, 2003, 5, 133-142).

| Cancer type | Bcl-2 over-expression (%) | Bcl-xL over-expression (%) |
|---|---|---|
| Prostate | 20-40 | 100 |
| -hormone resistant | 80-100 | — |
| Breast | 60-80 | 40-60 |
| Non-small cell lung | 20-40 | — |
| Small cell lung | 60-80 | — |
| Colorectal | 50-100 | 83 |
| Melanoma | 65 | 90 |
| Multiple myeloma (at relapse) | — | 77 |
| Head and Neck | 13 | 52-75 |
| Pancreatic | 23 | 90 |
| Hepatocellular carcinoma | — | 80 |

Biological approaches to modulating Bcl-2 function using anti-sense oligonucleotides or single-chain antibodies have been shown to enhance tumor cell chemosensitivity (Ziegler, A.; Luedke, G. H.; Fabbro, D.; Altmann, K. H.; Stahel, R. A.; Zangemeister-Wittke, U. Induction of apoptosis in small-cell lung cancer cells by an antisense oligodeoxynucleotide targeting the Bcl-2 coding sequence. J. Natl. Cancer. Inst. 1997, 89, 1027-1036; Webb, A.; Cunningham, D.; Cotter, F.; Clarke, P. A.; Di Stefano, F.; Ross, P.; Corpo, M.; Dziewanowska, Z. Bcl-2 antisense therapy in patients with non-hodgkin lymphoma. Lancet 1997, 349, 1137-1141; Cotter, F. E. Phase I clinical and pharmacokinetic study of Bcl-2 antisense oligonucleotide therapy in patients with non-hodgkin's lymphoma. J. Clin. Oncol. 2000, 18, 1812-1823; Piche, A.; Grim, J.; Rancourt, C.; Gomez-Navarro, J.; Reed, J. C.; Curiel, D. T. Modulation of Bcl-2 protein levels by an intracellular anti-Bcl-2 single-chain antibody increases drug-induced cytotoxicity in the breast cancer cell line MCF-7. Cancer Res. 1998, 58, 2134-2140).

It has been shown that an anti-sense oligonucleotide (G3139) (Raynaud, F. I.; Orr, R. M.; Goddard, P. M.; Lacey, H. A.; Lancashire, H.; Judson, I. R.; Beck, T.; Bryan, B.; Cotter, F. E. Pharmacokinetics of G3139, a phosphorothioate oligodeoxynucleotide antisense to Bcl-2, after intravenous administration or continuous subcutaneous infusion to mice. J. Pharmacol. Exp. Ther. 1997, 281, 420-427), designed to hybridize to sequence in Bcl-2 mRNA, inhibits Bcl-2 expression, induces apoptosis and inhibits cell growth in human breast cancer cells having Bcl-2 over-expression (Chen, H. X., Marchall, J. L., Trocky, N., Baidas, S., Rizvi, N., Ling, Y., Bhagava, P., Lippman, M. E., Yang, D., and Hayes, D. F. A Phase I study of Bcl-2 antisense G3139 (Genta) and weekly docetaxel in patients with advanced breast cancer and other solid tumors. Proceedings of American Society of Clinical Oncology, 2000). Importantly, synergistic effects and complete tumor regression were observed in vivo in the combined treatments of G3139 with docetaxel. Therefore, Bcl-2 represents a highly attractive target for the development of a novel therapy for the treatment of many forms of cancers.

Limitations associated with the use of large molecules, such as oligonucleotides, proteins and polypeptides, as therapeutic agents include poor oral availability, poor in vivo stability, and high cost. More desirable therapeutics would be non-peptide, cell-permeable small molecules that bind to Bcl-2 and block the anti-apoptotic function in cancer and promote cell-death in tumors.

Various small molecules have been shown to inhibit the function of Bcl-2. For example, acyl sulfonamides were shown to inhibit the function of Bcl-2 and Bcl-xL in biochemical and in vitro assays. *Nature* (2005) 435, 677-681. Nevertheless, the need exists for additional small organic molecules that bind to Bcl-2 and block its anti-apoptotic function in cancer and promote cell death in tumors. The present invention fulfills this need and has other related advantages.

SUMMARY OF THE INVENTION

One aspect of the present invention relates to isoxazolidine compounds. In certain instances, the nitrogen atom of the isoxazolidine ring is bonded to a substituted aralkyl group. In certain instances, the substituted aralkyl group is a substituted benzyl group. In certain instances, the isoxazolidine ring is substituted with a hydroxy methyl or hydroxy ethyl group. In certain instances, the isoxazolidine ring is substituted with a hydroxy methyl and a hydroxy ethyl group. In certain instances, the isoxazolidine ring is substituted with an amide group. The present invention further provides pharmaceutically active salts of the above-mentioned isoxazolidine compounds. Another aspect of the present invention relates to pharmaceutical compositions comprising an isoxazolidine compound of the invention. Another aspect of the present invention relates to a method of using the above compounds, or pharmaceutically active salts thereof, alone or in combination with other agents to treat cancer. Specifically, the invention provides a therapeutic method comprising treating a condition characterized by the pathological proliferation of mammalian cells, such as tumors cells, (e.g., breast cancer and myeloid leukemia), by administering to a mammal or a human afflicted with such a condition an effective amount of a compound of the present invention. In certain instances, the compound of the present invention is administered with a pharmaceutically acceptable carrier.

DETAILED DESCRIPTION OF THE INVENTION

The present invention generally relates to isoxazolidine compounds useful for treating cancer. The isoxazolidine compounds of the invention bind to one or more Bcl proteins and block Bcl anti-apoptotic function in cancer cells and tumor tissue that express the Bcl protein. In certain embodiments, certain compounds of the invention selectively inhibit the anti-apoptotic activity of only one member of the Bcl-2 subfamily of anti-apoptotic proteins. The isoxazolidine compounds of the invention can be used to treat a patient suffering from a disease related to Bcl. In certain instances, the isoxazolidine compounds of the invention are used to treat a patient suffering from cancer. The isoxazolidine compounds of the invention can be administered to a patient in the form of a pharmaceutical composition. The pharmaceutical composition comprises an isoxazolidine compound of the invention and one or more pharmaceutically acceptable excipients. In certain instances, the pharmaceutical composition comprises an isoxazolidine compound of the invention, a chemotherapeutic agent, and one or more pharmaceutically acceptable excipients. In certain instances, the chemotherapeutic agent is Docetaxel, Paclitaxel, cisplatin, 5-FU, Doxrubincin, epipodophyllotoxin, camptothecin, 17-AAG, or cyclophosphamide.

Synthesis of Isoxazolidine Compounds

The isoxazolidine compounds of the invention can be prepared using a [3+2] cycloaddition reaction between a nitrone and an alkene. The nitrone substrate and alkene may contain functional groups suitable for chemical derivatization following synthesis of the isoxazolidine core. In certain instances, a Lewis acid is added to the reaction. In a preferred embodiment, the Lewis acid is $Ti(Oi-Pr)_4$. In certain instances, the reaction mixture is subjected to microwave radiation. In general, the subject reactions are carried out in a liquid reaction medium, but can be carried out on a solid support. The reactions may be conducted in an aprotic solvent, preferably one in which the reaction ingredients are substantially soluble. Suitable solvents include ethers, such as diethyl ether, 1,2-dimethoxyethane, diglyme, t-butyl methyl ether, tetrahydrofuran and the like; halogenated solvents, such as chloroform, dichloromethane, dichloroethane, chlorobenzene, carbon tetrachloride, and the like; aliphatic or aromatic hydrocarbon solvents, such as benzene, xylene, toluene, hexane, pentane and the like; esters and ketones, such as ethyl acetate, acetone, and 2-butanone; polar aprotic solvents, such as acetonitrile, dimethylsulfoxide, dimethylformamide, pyridine, and the like; or combinations of two or more solvents. The reactions can be conducted at a variety of temperatures. Generally, reactions conducted at lower temperatures will take a longer to reach completion. In certain instances, the cycloaddition reaction is conducted in the range of about 15° C. to about 60° C. In certain instances, the cycloaddition reaction is conducted in the range of about 15° C. to about 30° C. In certain instances, the cycloaddition reaction is conducted at about room temperature. In certain instances, the cycloaddition reaction is conducted in the range of about 80° C. to about 150° C. In certain instances, the cycloaddition reaction is conducted in the range of about 90° C. to about 120° C. In certain instances, the cycloaddition reaction is conducted in the range of about 95° C. to about 105° C. In certain instances, the cycloaddition reaction is conducted using a substrate attached to a solid support. Following synthesis of the isoxazolidine core, the isoxazolidine compound may be derivatized using a variety of functionalization reactions known in the art. Representative examples include palladium coupling reactions to alkenylhalides or aryl halides, oxidations, reductions, reactions with nucleophiles, reactions with electrophiles, pericyclic reactions, installation of protecting groups, removal of protecting groups, and the like.

Biological Activity Analysis

The following in vitro binding and cellular assays can be used to determine the activity and specificity of compounds of the present invention to bind to Bcl-2 and inhibit Bcl-2 function in a cell.

Bcl-2 Binding Assay

Bcl-2 and Bcl-xL binding can be determined using a variety of known methods. One such assay is a sensitive and quantitative in vitro binding assay using fluorescence polarization (FP) described by Wang, J.-L.; Zhang, Z-J.; Choksi, S.; Sjam. S.; Lu, Z.; Croce, C. M.; Alnemri, E. S.; Komgold, R.; Huang, Z. Cell permeable Bcl-2 binding peptides: a chemical approach to apoptosis induction in tumor cells. Cancer Res. 2000, 60, 1498-1502).

Cell Based Assays

The ability of isoxazolidine compounds of the present invention to inhibit cell-viability in cancer cells with Bcl-2 protein over-expression was demonstrated. When RL-cells are exposed to isoxazolidine compounds of the present invention, the inhibitors show a dose-dependent cell-killing in the Alamar blue cytoxicity assay with $IC_{50}$ values of from about 100 µM to about 1 µM (See Examples). When Panc1 cells are exposed to the isoxazolidine compounds of the present invention in combination with camptothecin, the inhibitors show a synergistic dose-dependent cell killing in the propidium iodide exclusion cell survival assay with $IC_{50}$ values of from about 100 µM to about 1 µM (See Examples).

Bcl-2 inhibitors have been shown to be active against a number of cancer cell lines as single agent, including, but not limited to, breast cancer (US 2003/0119894, published PCT applications WO 02/097053 and WO 02/13833), lymphomas (Nature (2005) 435, 677-681), small cell lung cancer (Nature (2005) 435, 677-681), head and neck cancer (published PCT application WO 02/097053), and leukemias (published PCT application WO 02/13833).

Bcl-2 inhibitors have been shown to be active against a number of cancer cell lines in combination with other anticancer agents and radiation, including, but not limited to, breast cancer (With docetaxel, published PCT application WO 02/097053), prostate cancer (With docetaxel, published PCT application WO 02/097053), head and neck cancer (With docetaxel, published PCT application WO 02/097053), and non small-cell lung cancer (With paclitaxel, Nature (2005) 435, 677-681). In addition to the aforementioned combination chemotherapeutics, small molecule inhibitors of Bcl-2 proteins display synergy with other anticancer agents, including, but not limited to etoposide, doxorubicin, cisplatin, paclitaxel, and radiation (Nature (2005) 435, 677-681).

Methods of Therapy and Treatment

The present invention further provides methods for treating and reducing the severity of cancer as well as other Bcl mediated disorders or conditions.

Cancers or neoplastic diseases and related disorders that can be treated by administration of compounds and compositions of the present invention, include, but are not limited to those listed in Table 1 (for a review of such disorders, see Fishman et al., 1985, Medicine, 2d Ed., J. B. Lippincott Co., Philadelphia):

TABLE 1

CANCERS AND NEOPLASTIC DISORDERS

Leukemia
    acute leukemia
    acute lymphocytic leukemia
    acute myelocytic leukemia
        myeloblastic
        promyelocytic
        myelomonocytic
        monocytic
        erythroleukemia
    chronic leukemia
    chronic myelocytic (granulocytic) leukemia TABLE 1-continued

CANCERS AND NEOPLASTIC DISORDERS chronic lymphocytic leukemia
Polycythemia vera
Lymphoma
    Hodgkin's disease
    non-Hodgkin's disease
Multiple myeloma
Waldenstrom's macroglobulinemia
Heavy chain disease
Solid tumors
    sarcomas and carcinomas
        fibrosarcoma
        myxosarcoma
        liposarcoma
        chondrosarcoma
        osteogenic sarcoma
        chordoma
        angiosarcoma
        lymphangiosarcoma
        lymphangioendotheliosarcoma
        synovioma
        mesothelioma
        Ewing's tumor
        leiomyosarcoma
        rhabdomyosarcoma
        colon carcinoma
        pancreatic cancer
        breast cancer
        ovarian cancer
        prostate cancer
        squamous cell carcinoma
        basal cell carcinoma
        adenocarcinoma
        sweat gland carcinoma
        sebaceous gland carcinoma
        papillary carcinoma
        papillary adenocarcinomas
        cystadenocarcinoma
        medullary carcinoma
        bronchogenic carcinoma
        renal cell carcinoma
        hepatoma
        bile duct carcinoma
        choriocarcinoma
        seminoma
        embryonal carcinoma
        Wilms' tumor
        cervical cancer
        uterine cancer
        testicular tumor
        lung carcinoma
        small cell lung carcinoma
        bladder carcinoma
        epithelial carcinoma
        glioma
        astrocytoma
        medulloblastoma
        craniopharyngioma
        ependymoma
        pinealoma
        hemangioblastoma
        acoustic neuroma
        oligodendroglioma
        meningioma
        melanoma
        neuroblastoma
        retinoblastoma In a preferred embodiment, the compounds of the present invention are used to treat cancers including, but not limited to lymphomas (preferably follicular lymphoma, diffuse large B-cell lymphoma, mantle cell lymphoma, or chronic lymphocytic leukemia), prostate cancer (more preferably hormone insensitive), breast cancer (preferably estrogen receptor positive), neuroblastoma, colorectal, endometrial, ovarian, lung (preferably small cell), hepatocellular carcinoma, multiple myeloma, head and neck or testicular cancer (preferably germ cell).

Treatment of Cancer in Combination with Chemotherapy or Radiotherapy

In certain embodiments, one or more compounds of the present invention are used to treat or prevent cancer or neoplastic disease in combination with one or more anti-cancer, chemotherapeutic agents including, but not limited to, methotrexate, taxol, mercaptopurine, thioguanine, hydroxyurea, cytarabine, cyclophosphamide, ifosfamide, nitrosoureas, cisplatin, carboplatin, mitomycin, dacarbazine, procarbizine, etoposides, prednisolone, dexamethasone, cytarbine, campathecins, bleomycin, doxorubicin, idarubicin, daunorubicin, dactinomycin, plicamycin, mitoxantrone, asparaginase, vinblastine, vincristine, vinorelbine, paclitaxel, and docetaxel. In a preferred embodiment, one or more compound of the present invention is used to treat or prevent cancer or neoplastic disease in combination with one or more chemotherapeutic or other anti-cancer agents including, but not limited to those presented in Table 2.

TABLE 2

CHEMOTHERAPEUTICS AND OTHER ANTI-CANCER AGENTS

| | |
|---|---|
| Radiation: | γ-radiation |
| Alkylating agents | |
| Nitrogen mustards: | cyclophosphamide |
| | Ifosfamide |
| | trofosfamide |
| | Chlorambucil |
| | Estramustine |
| | melphalan |
| Nitrosoureas: | carmustine (BCNU) |
| | Lomustine (CCNU) |
| Alkylsulphonates | busulfan |
| | Treosulfan |
| Triazenes: | Dacarbazine |
| Platinum containing compounds: | Cisplatin |
| | carboplatin |
| | oxaplatin |
| Plant Alkaloids | |
| Vinca alkaloids: | vincristine |
| | Vinblastine |
| | Vindesine |
| | Vinorelbine |
| Taxoids: | paclitaxel |
| | Docetaxol |
| DNA Topoisomerase Inhibitors | |
| Epipodophyllins: | etoposide |
| | Teniposide |
| | Topotecan |
| | 9-aminocamptothecin |
| | campto irinotecan |
| | crisnatol |
| mytomycins | |
| mytomycin C | Mytomycin C |
| Anti-metabolites | |
| Anti-folates: | |
| DHFR inhibitors: | methotrexate |
| | Trimetrexate |
| IMP dehydrogenase Inhibitors: | mycophenolic acid |
| | Tiazofurin |
| | Ribavirin |
| | EICAR |
| Ribonucleotide reductase Inhibitors: | hydroxyurea |
| | deferoxamine |

TABLE 2-continued

CHEMOTHERAPEUTICS AND OTHER ANTI-CANCER AGENTS

| | |
|---|---|
| Pyrimidine analogs: | |
| Uracil analogs | 5-Fluorouracil |
| | Floxuridine |
| | Doxifluridine |
| | Ratitrexed |
| | capecitabine |
| Cytosine analogs | cytarabine (ara C) |
| | Cytosine arabinoside |
| | fludarabine |
| Purine analogs: | mercaptopurine |
| | Thioguanine |
| Hormonal therapies: | |
| Receptor antagonists: | |
| Anti-estrogens | Tamoxifen |
| | Raloxifene |
| | megestrol |
| LHRH agonists: | goscrclin |
| | Leuprolide acetate |
| Anti-androgens: | flutamide |
| | bicalutamide |
| Retinoids/Deltoids | |
| Vitamin D3 analogs: | EB 1089 |
| | CB 1093 |
| | KH 1060 |
| Photodyamic therapies: | vertoporfin (BPD-MA) |
| | Phthalocyanine |
| | photosensitizer Pc4 |
| | Demethoxy-hypocrellin A |
| | (2BA-2-DMHA) |
| Cytokines: | Interferon α |
| | Interferon γ |
| | Tumor necrosis factor |
| Others: | |
| Isoprenylation inhibitors: | Lovastatin |
| Dopaminergic neurotoxins: | 1-methyl-4-phenylpyridinium ion |
| Cell cycle inhibitors: | staurosporine |
| Actinomycins: | Actinomycin D |
| | Dactinomycin |
| Bleomycins: | bleomycin A2 |
| | Bleomycin B2 |
| | Peplomycin |
| Anthracyclines: | daunorubicin |
| | Doxorubicin (adriamycin) |
| | Idarubicin |
| | Epirubicin |
| | Pirarubicin |
| | Zorubicin |
| | Mitoxantrone |
| MDR inhibitors: | verapamil |
| $Ca^{2+}$ ATPase inhibitors: | thapsigargin |
| Antibodies | Avastin |
| | Erbitux |
| | Rituxan |
| Others | Prednisilone |
| | Imatinib |
| | Thalidomide |
| | Lenalidomide |
| | Bortezomib |
| | Gemcitabine |
| | Erlotinib |
| | Gefitinib |
| | Sorafenib |
| | Sutinib |

The chemotherapeutic agent and/or radiation therapy can be administered according to therapeutic protocols well known in the art. It will be apparent to those skilled in the art that the administration of the chemotherapeutic agent and/or radiation therapy can be varied depending on the disease being treated and the known effects of the chemotherapeutic agent and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., antineoplastic agent or radiation) on the patient, and in view of the observed responses of the disease to the administered therapeutic agents.

Also, in general, compounds of the present invention and the chemotherapeutic agent do not have to be administered in the same pharmaceutical composition, and may, because of different physical and chemical characteristics, have to be administered by different routes. For example, compounds of the present invention may be administered intravenously to generate and maintain good blood levels, while the chemotherapeutic agent may be administered orally. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of chemotherapeutic agent or radiation will depend upon the diagnosis of the attending physicians and their judgment of the condition of the patient and the appropriate treatment protocol.

A compound of the present invention, and chemotherapeutic agent and/or radiation may be administered concurrently (e.g., simultaneously, essentially simultaneously or within the same treatment protocol) or sequentially, depending upon the nature of the proliferative disease, the condition of the patient, and the actual choice of chemotherapeutic agent and/or radiation to be administered in conjunction (i.e., within a single treatment protocol) with a compound of the present invention.

If a compound of the present invention, and the chemotherapeutic agent and/or radiation are not administered simultaneously or essentially simultaneously, then the optimum order of administration of the compound of the present invention, and the chemotherapeutic agent and/or radiation, may be different for different tumors. Thus, in certain situations the compound of the present invention may be administered first followed by the administration of the chemotherapeutic agent and/or radiation; and in other situations the chemotherapeutic agent and/or radiation may be administered first followed by the administration of a compound of the present invention. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient. For example, the chemotherapeutic agent and/or radiation may be administered first, especially if it is a cytotoxic agent, and then the treatment continued with the administration of a compound of the present invention followed, where determined advantageous, by the administration of the chemotherapeutic agent and/or radiation, and so on until the treatment protocol is complete.

Thus, in accordance with experience and knowledge, the practicing physician can modify each protocol for the administration of a component (therapeutic agent, i.e., compound of the present invention, chemotherapeutic agent or radiation) of the treatment according to the individual patient's needs, as the treatment proceeds.

DEFINITIONS

For convenience, certain terms employed in the specification, examples, and appended claims are collected here.

The terms "co-administration" and "co-administering" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent at the same time.

The term "heteroatom" as used herein means an atom of any element other than carbon or hydrogen. Preferred heteroatoms are boron, nitrogen, oxygen, phosphorus, sulfur and selenium.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 or fewer. Likewise, preferred cycloalkyls have from 3-10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "haloalkyl", as used herein, refers to an alkyl group where anywhere from 1 to all hydgrogens have been replaced with a halide. A "perhaloalkyl" is where all of the hydrogens have been replaced with a halide.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

The term "aryl" as used herein includes 5-, 6- and 7-membered single-ring aromatic groups that may include from zero to four heteroatoms, for example, benzene, anthracene, naphthalene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, $-CF_3$, $-CN$, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, $-CF_3$, $-CN$, or the like.

As used herein, the term "nitro" means $-NO_2$; the term "halogen" designates $-F$, $-Cl$, $-Br$ or $-I$; the term "sulfhydryl" means $-SH$; the term "hydroxyl" means $-OH$; and the term "sulfonyl" means $-SO_2-$.

The terms "amine" and "amino" are art-recognized and refer to both unsubstituted and substituted amines, e.g., a moiety that may be represented by the general formulas:

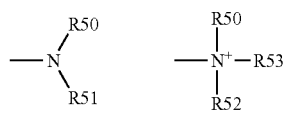

wherein R50, R51 and R52 each independently represent a hydrogen, an alkyl, an alkenyl, $-(CH_2)_m-R61$, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In certain embodiments, only one of R50 or R51 may be a carbonyl, e.g., R50, R51 and the nitrogen together do not form an imide. In other embodiments, R50 and R51 (and optionally R52) each independently represent a hydrogen, an alkyl, an alkenyl, or $-(CH_2)_m-R61$. Thus, the term "alkylamine" includes an amine group, as defined above, having a substituted or unsubstituted alkyl attached thereto, i.e., at least one of R50 and R51 is an alkyl group.

The term "acylamino" is art-recognized and refers to a moiety that may be represented by the general formula:

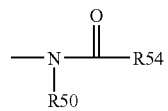

wherein R50 is as defined above, and R54 represents a hydrogen, an alkyl, an alkenyl or $-(CH_2)_m-R61$, where m and R61 are as defined above.

The term "amido" is art recognized as an amino-substituted carbonyl and includes a moiety that may be represented by the general formula:

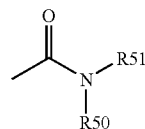

wherein R50 and R51 are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of $-S-alkyl$, $-S-alkenyl$, $-S-alkynyl$, and $-S-(CH_2)_m-R61$, wherein m and R61 are defined above. Representative alkylthio groups include methylthio, ethyl thio, and the like.

The term "carboxyl" is art recognized and includes such moieties as may be represented by the general formulas:

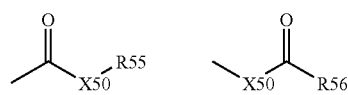

wherein X50 is a bond or represents an oxygen or a sulfur, and R55 and R56 represents a hydrogen, an alkyl, an alkenyl, $-(CH_2)_m-R61$ or a pharmaceutically acceptable salt, R56 represents a hydrogen, an alkyl, an alkenyl or $-(CH_2)_m-R61$, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art recognized and includes a moiety that can be represented by the general formula:

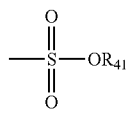

in which $R_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The term "carbamoyl" refers to —O(C=O)NRR', where R and R' are independently H, aliphatic groups, aryl groups or heteroaryl groups.

The term "alkylamino" refers to —NHR, where R is an alkyl group.

The term "dialkylamino" refers to —NRR', where both R and R' are alkyl groups.

The term "hydroxyalkyl" refers to —R—OH, where R is an aliphatic group.

The term "aminoalkyl" refers to —R—$NH_2$, where R is an aliphatic group.

The term "alkylaminoalkyl" refers to —R—NH—R', where both R and R' are aliphatic groups.

The term "dialkylaminoalkyl" refers to —R—N(R')—R", where R, R', and R" are aliphatic groups.

The term "arylaminoalkyl" refers to —R—NH—R', where R is an aliphatic and R' is an aryl group.

The term "oxo" refers to a carbonyl oxygen (=O).

The term "diradical" or "bivalent" as used herein are used interchangeably and refer to any of a series of divalent groups from alkyl, alkenyl, alkynyl, alkylamino, alkoxyl, cycloalkyl, heterocycloalkyl, aryl, aralkyl, heterocyclyl, heteroaryl, and heteroaralkyl groups. For example,

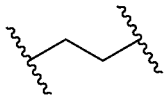

is a bivalent alkyl or alkyl diradical;

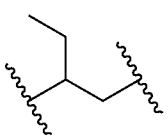

is also a bivalent alkyl or alkyl diradical;

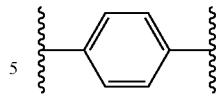

is a bivalent aryl or aryl diradical;

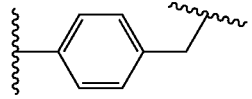

is a bivalent aralkyl or aralkyl diradical; and

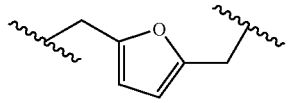

is a bivalent (alkyl)heteroaralkyl or (alkyl)heteroaralkyl diradical.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The term "sulfate" is art recognized and includes a moiety that can be represented by the general formula:

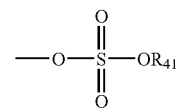

in which $R_{41}$ is as defined above.

The term "sulfonylamino" is art recognized and includes a moiety that can be represented by the general formula:

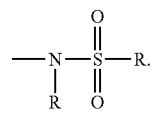

The term "sulfamoyl" is art-recognized and includes a moiety that can be represented by the general formula:

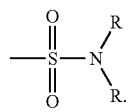

The term "sulfonyl", as used herein, refers to a moiety that can be represented by the general formula:

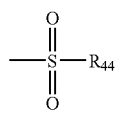

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

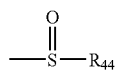

in which $R_{44}$ is selected from the group consisting of hydrogen, alkyl, alkenyl, alkynyl, cycloalkyl, heterocyclyl, aralkyl, or aryl.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_7$, m and $R_7$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g., alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991). Protected forms of the inventive compounds are included within the scope of this invention.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., functioning as analgesics), wherein one or more simple variations of substituents are made which do not adversely affect the efficacy of the compound in binding to sigma receptors. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986-87, inside cover.

The term "subject" as used herein, refers to an animal, typically a mammal or a human, that has been the object of treatment, observation, and/or experiment. When the term is used in conjunction with administration of a compound or drug, then the subject has been the object of treatment, observation, and/or administration of the compound or drug.

The term "therapeutically effective amount" as used herein, means that amount of active compound or pharmaceutical agent that elicits the biological or medicinal response in a cell culture, tissue system, animal, or human that is being sought by a researcher, veterinarian, clinician, or physician, which includes alleviation of the symptoms of the disease, condition, or disorder being treated. In the present invention, such an amount will be sufficient to bind to bcl-2 in a cell and inhibit at least part of the anti-apoptotic activity of the protein. Such an amount may be sufficient to provide therapeutic effectiveness in a patient or may serve to sensitize the cell to treatment with another anticancer agent.

The term "composition" is intended to encompass a product comprising the specified ingredients in the specified amounts, as well as any product that results, directly or indirectly, from combinations of the specified ingredients in the specified amounts.

The term "pharmaceutically acceptable carrier" refers to a medium that is used to prepare a desired dosage form of a compound. A pharmaceutically acceptable carrier can include one or more solvents, diluents, or other liquid vehicles; dispersion or suspension aids; surface active agents; isotonic agents; thickening or emulsifying agents; preservatives; solid binders; lubricants; and the like. Remington's Pharmaceutical Sciences, Fifteenth Edition, E. W. Martin (Mack Publishing Co., Easton, Pa., 1975) and Handbook of Pharmaceutical Excipients, Third Edition, A. H. Kibbe ed. (American Pharmaceutical Assoc. 2000), disclose various carriers used in formulating pharmaceutical compositions and known techniques for the preparation thereof.

The phrases "Bcl-mediated disorder" and "disorder mediated by cells expressing Bcl proteins" refer to pathological and disease conditions in which a Bcl protein plays a role. Such roles can be directly related to the pathological condition or can be indirectly related to the condition. The feature common to this class of conditions is that they can be ameliorated by inhibiting the activity of, function of, or association with Bcl proteins.

As used herein, the terms "Bcl" and "Bcl protein" are intended to encompass one or more of the Bcl-2 subfamily of anti-apoptotic proteins Bcl-2, Bcl-w, Mcl-1, Bcl-XL, A1, Bfl1, Bcl-B, BOO/DIVA, and their homologues.

Compounds of the Invention

In certain embodiments, the present invention relates to a compound of formula 1:

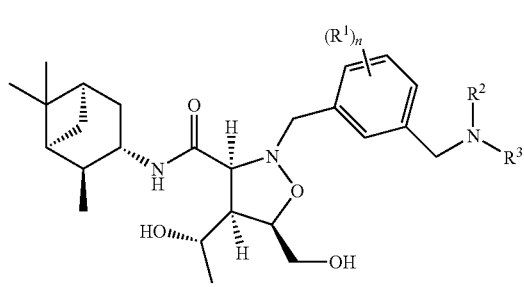

1 or a pharmaceutically acceptable salt thereof;
wherein independently for each occurrence;
n is 0, 1, 2, 3, or 4;
$R^1$ independently for each occurrence is H, alkyl, alkenyl, alkynyl, aryl, aralkyl, heterocyclyl, heterocyclylalkyl, heteroaryl, heteroaralky, halide, hydroxyl, alkoxyl, aryloxy, acyloxy, amino, alkylamino, arylamino, acylamino, aralkylamino, nitro, acylthio, carboxamide, carboxyl, nitrile, —$COR^5$, —$CO_2R^5$, —$N(R^5)CO_2R^6$, —$OC(O)N(R^5)(R^6)$, —$N(R^5)SO_2R^6$, or —$N(R^5)C(O)N(R^5)(R^6)$;

$R^2$ and $R^3$ independently for each occurrence are H, alkyl, alkenyl, alkynyl, aryl, aralkyl, heterocyclyl, heterocyclylalkyl, heteroaryl, heteroaralkyl, or —$[C(R^5)(R^6)]_p$—$R^4$; or has the formula 1a

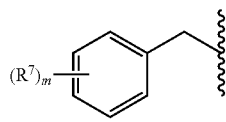

1a wherein
m is 0, 1, 2, 3, 4, or 5;
$R^7$ for each occurrence independently is H, alkyl, aryl, alkenyl, halide, hydroxyl, alkoxyl, alkenyloxy, aryloxy, acyloxy, amino, alkylamino, arylamino, acylamino, aralkylamino, nitro, acylthio, carboxamide, carboxyl, nitrile, —$OSO_3R^5$, —$SO_2R^5$, —$S(O)R^5$, —$SR^5$, —$PO_2R^5$, —$OPO_2R^5$, —$COR^5$, —$CO_2R^5$, —$OCH_2CO_2R^5$, or —$OCH_2C(O)N(R^5)(R^6)$; or two occurrences of $R^7$ taken together may form a monocyclic ring between 5-8 ring atoms, of which, one, two, or three atoms are independently S, O, or N;

$R^4$ is halide, hydroxyl, alkoxyl, aryloxy, acyloxy, amino, alkylamino, arylamino, acylamino, aralkylamino, nitro, acylthio, carboxamide, carboxyl, nitrile, —$OSO_3R^5$, —$SO_2R^5$, —$S(O)R^5$, —$PO_2OR^5$, —$OPO_2OR^5$, —$COR^5$, —$CO_2R^5$, —$N(R^5)CO_2R^6$, —$OC(O)N(R^5)(R^6)$, —$N(R^5)SO_2R^6$, or —$N(R^5)C(O)N(R^5)(R^6)$; and each of $R^5$ and $R^6$ independently for each occurrence is H, alkyl, alkenyl, alkynyl, aryl, aralkyl, cycloalkyl, heterocyclyl, heterocyclylalkyl, heteroaryl, or heteroaralkyl; or $R^5$ and $R^6$ taken together form a monocyclic ring with 4-8 ring atoms, of which one, two, or three ring atoms are independently S, O, or N.

The present invention also relates to a compound selected from the group consisting of:

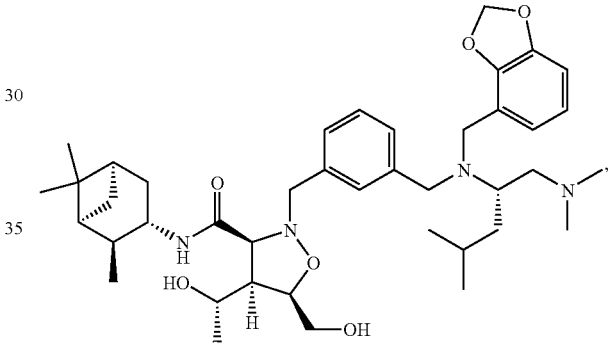

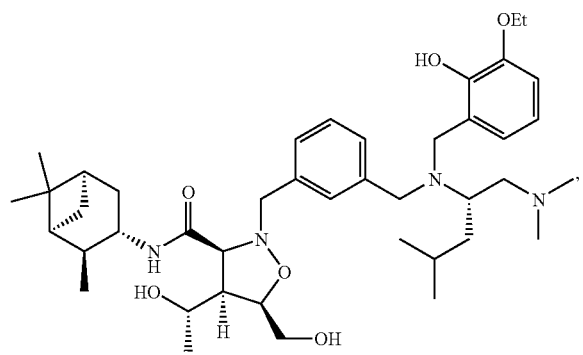

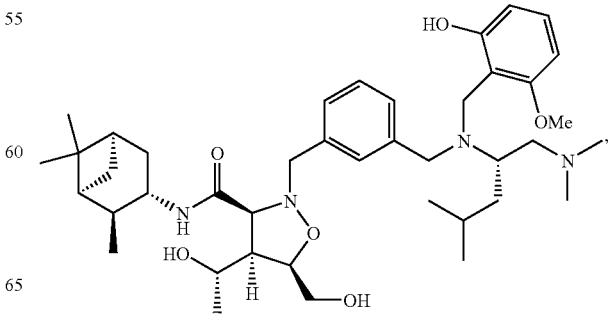

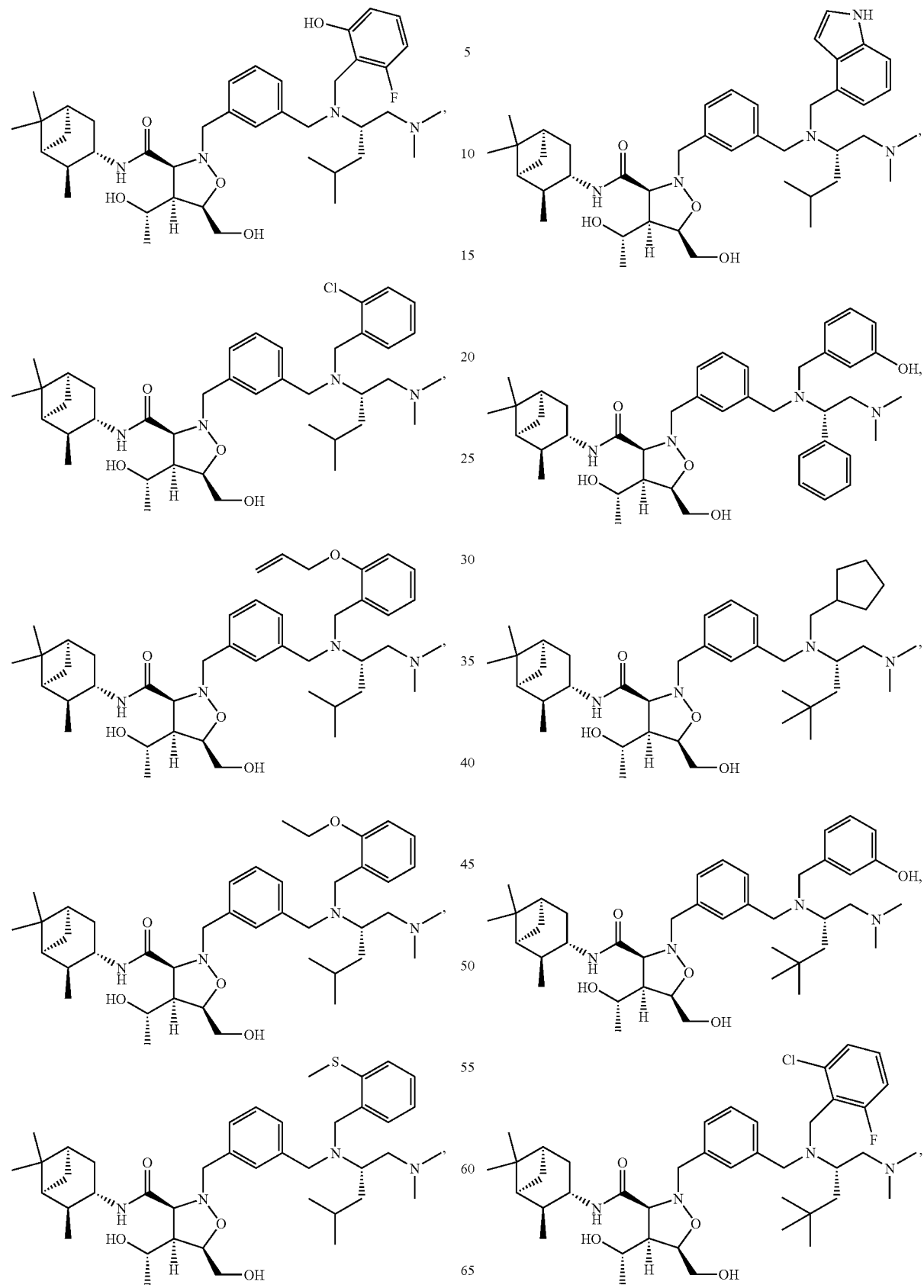

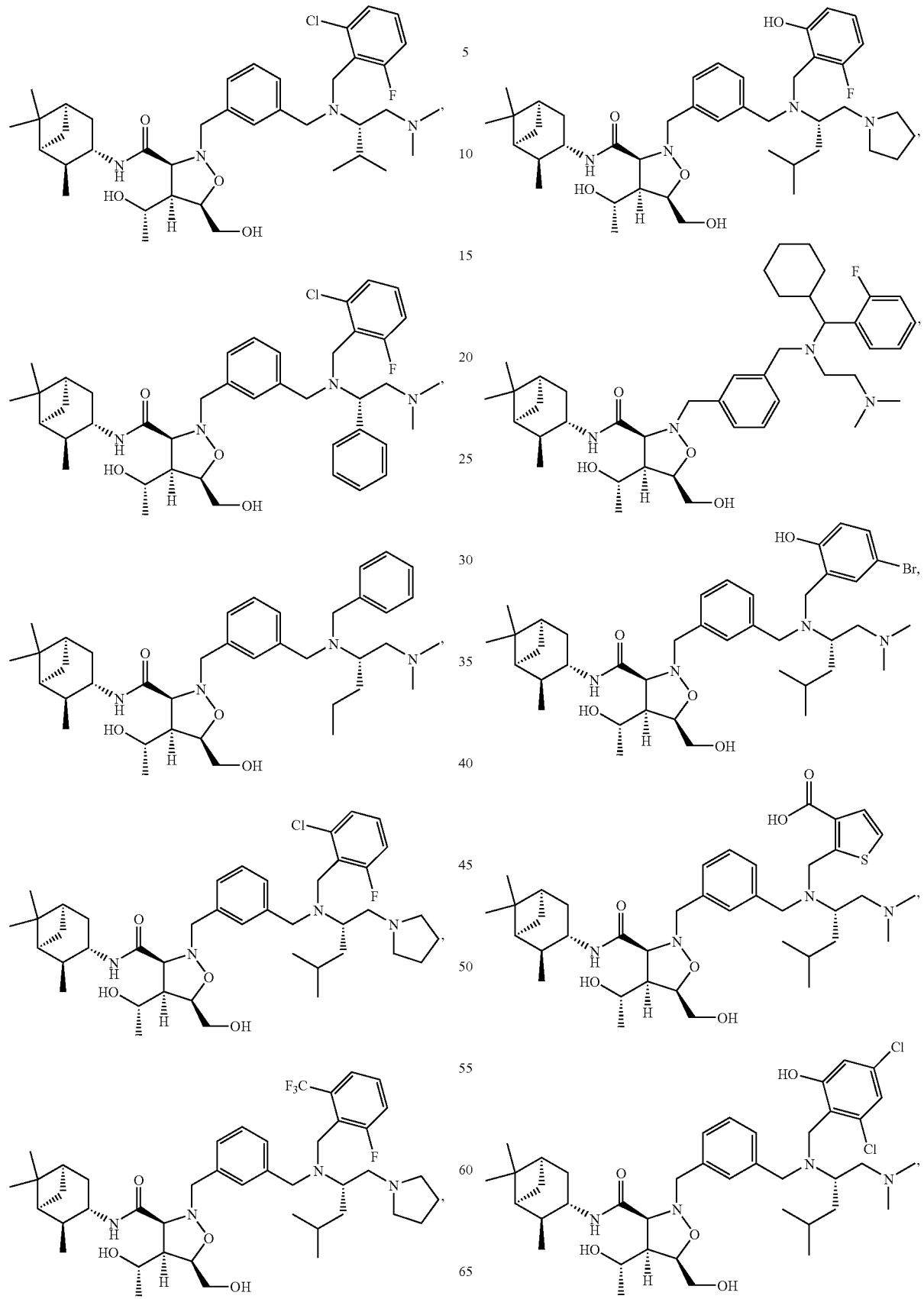

-continued
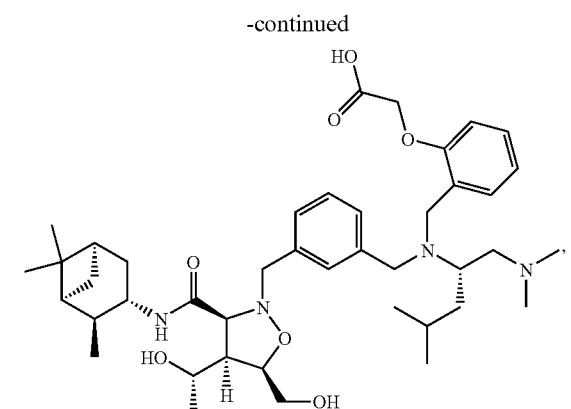
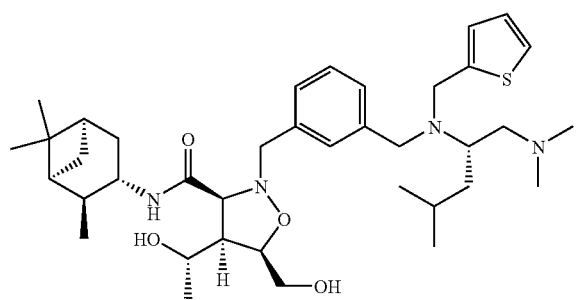
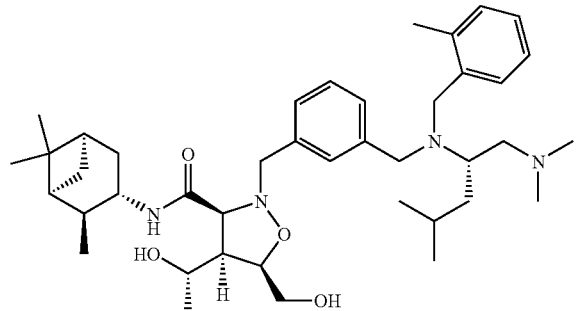
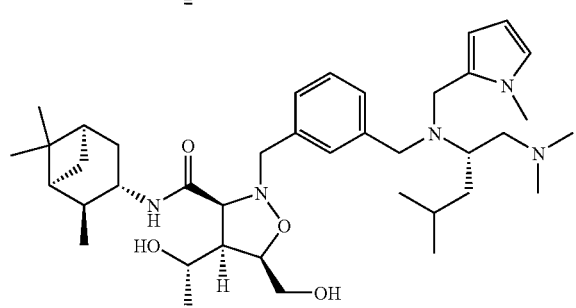
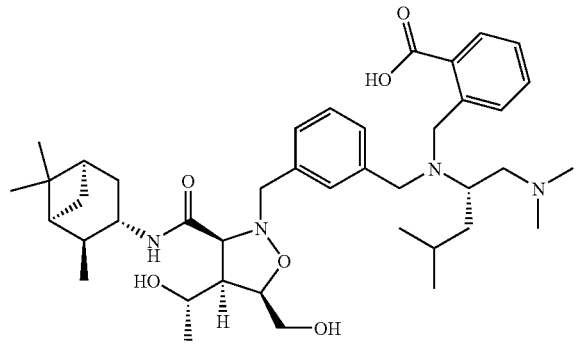
-continued
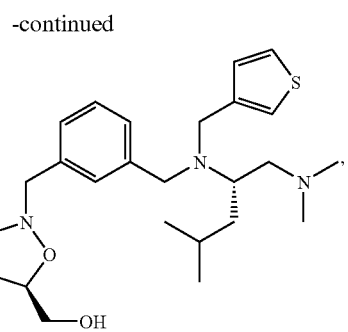
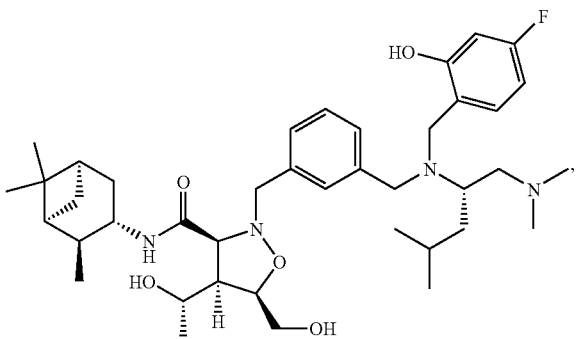
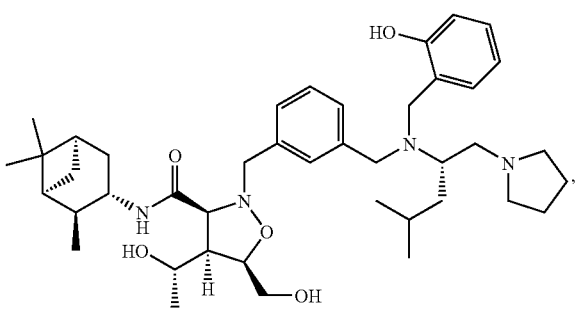
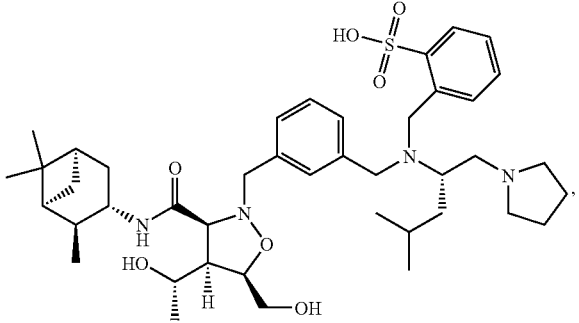
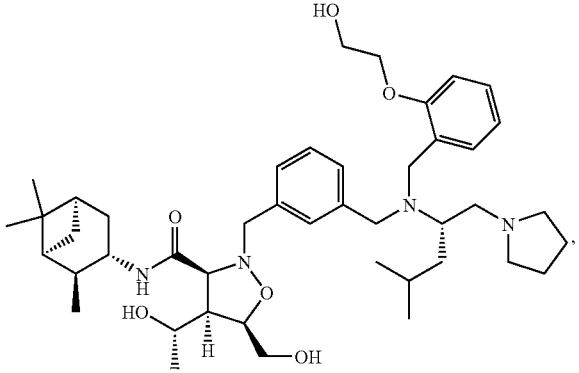

-continued

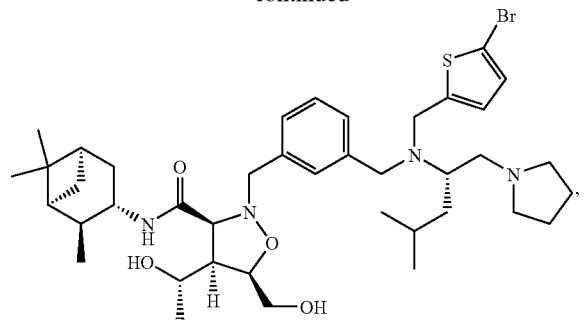

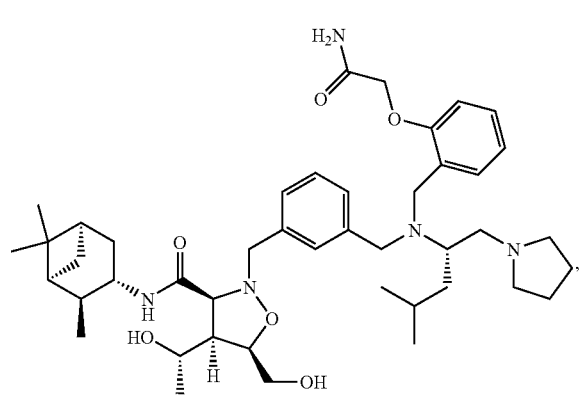

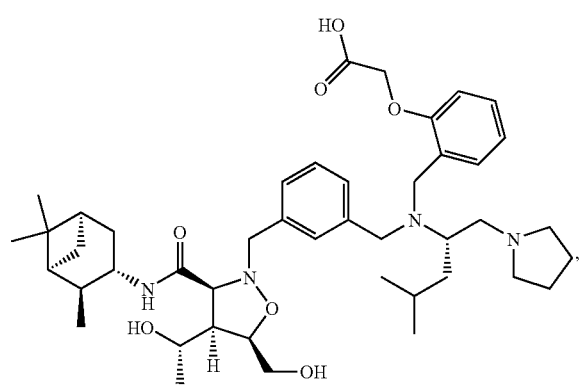

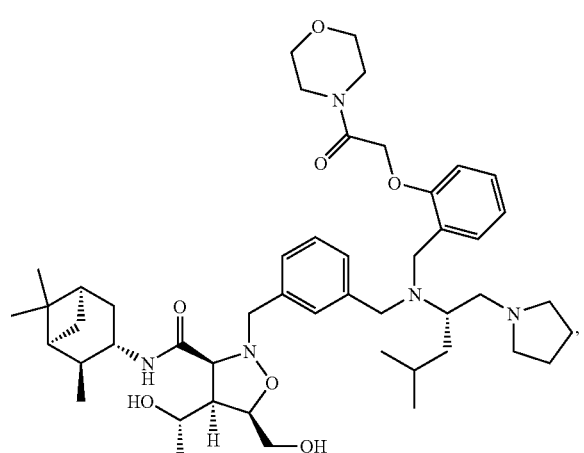

-continued

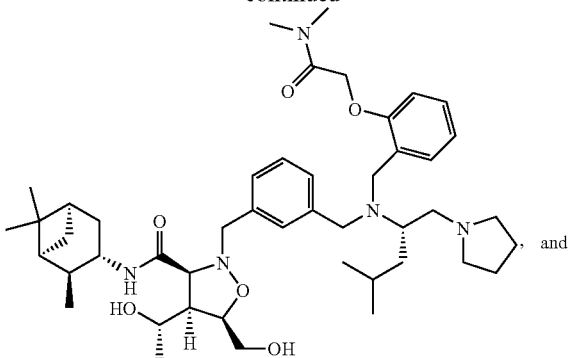
, and

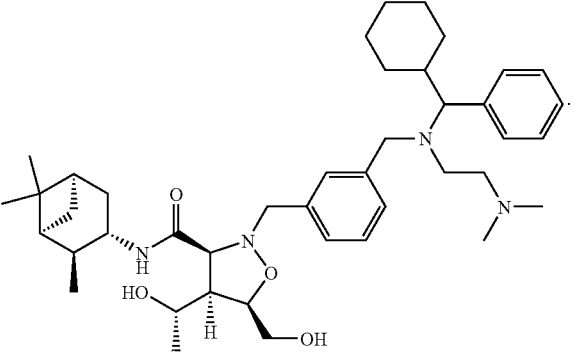

Another aspect of the present invention relates to a pharmaceutical composition comprising a compound as described above; and at least one pharmaceutically acceptable excipient.

Methods of the Invention

One aspect of the present invention relates to a method of treating a Bcl-mediated disorder, comprising the step of:

administering to a patient in need thereof a therapeutically effective amount of a compound described above.

In certain embodiments, the present invention relates to the aforementioned method, wherein said Bcl-mediated disorder is cancer or neoplastic disease.

In certain embodiments, the present invention relates to the aforementioned method, wherein said cancer or neoplastic disease is selected from the group consisting of acute leukemia, acute lymphocytic leukemia, acute myelocytic leukemia, myeloblastic, promyelocytic, myelomonocytic, monocytic, erythroleukemia, chronic leukemia, chronic myelocytic (granulocytic) leukemia, chronic lymphocytic leukemia, polycythemia Vera, Hodgkin's disease, non-Hodgkin's disease; multiple myeloma, Waldenstrom's macroglobulinemia, heavy chain disease, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, stadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, and endometrial cancer.

In certain embodiments, the present invention relates to the aforementioned method, wherein said cancer is follicular lymphoma, diffuse large B-cell lymphoma, mantle cell lymphoma, chronic lymphocytic leukemia prostrate cancer, breast cancer, neuroblastoma, colorectal, endometrial, ovarian, lung cancer, hepatocellular carcinoma, multiple myeloma, head and neck or testicular cancer.

In certain embodiments, the present invention relates to the aforementioned method, wherein said cancer over-expresses a Bcl protein.

In certain embodiments, the present invention relates to the aforementioned method, wherein said cancer is dependent upon a Bcl protein for growth and survival.

In certain embodiments, the present invention relates to the aforementioned method, wherein said Bcl protein is Bcl-2.

In certain embodiments, the present invention relates to the aforementioned method, wherein said Bcl protein is Bcl-xL.

In certain embodiments, the present invention relates to the aforementioned method, wherein the cancer exhibits a t(14; 18) chromosomal translocation.

In certain embodiments, the present invention relates to the aforementioned method, wherein said compound is administered parenterally.

In certain embodiments, the present invention relates to the aforementioned method, wherein said compound is administered intramuscularly, intravenously, subcutaneously, orally, pulmonary, intrathecally, topically or intranasally.

In certain embodiments, the present invention relates to the aforementioned method, wherein said compound is administered systemically.

In certain embodiments, the present invention relates to the aforementioned method, wherein said patient is a mammal.

In certain embodiments, the present invention relates to the aforementioned method, wherein said patient is a primate.

In certain embodiments, the present invention relates to the aforementioned method, wherein said patient is a human.

In another aspect, the present invention relates to a method of treating a Bcl-mediated disorder, comprising the step of: administering to a patient in need thereof a therapeutically effective amount of a chemothereutic agent in combination with a therapeutically effective amount of a compound of compound described above.

In certain embodiments, the present invention relates to the aforementioned method, wherein said Bcl-mediated disorder is cancer or neoplastic disease.

In certain embodiments, the present invention relates to the aforementioned method, wherein said cancer or neoplastic disease is selected from the group consisting of acute leukemia, acute lymphocytic leukemia, acute myelocytic leukemia, myeloblastic, promyelocytic, myelomonocytic, monocytic, erythroleukemia, chronic leukemia, chronic myelocytic (granulocytic) leukemia, chronic lymphocytic leukemia, polycythemia Vera, Hodgkin's disease, non-Hodgkin's disease; multiple myeloma, Waldenstrom's macroglobulinemia, heavy chain disease, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, stadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, and endometrial cancer.

In certain embodiments, the present invention relates to the aforementioned method, wherein the cancer over-expresses a Bcl protein.

In certain embodiments, the present invention relates to the aforementioned method, wherein said cancer is dependent upon a Bcl protein for growth and survival.

In certain embodiments, the present invention relates to the aforementioned method, wherein said Bcl protein is Bcl-2.

In certain embodiments, the present invention relates to the aforementioned method, wherein said Bcl protein is Bcl-xL.

In certain embodiments, the present invention relates to the aforementioned method, wherein said cancer exhibits a t(14; 18) chromosomal translocation.

In certain embodiments, the present invention relates to the aforementioned method, wherein the amount of compound described herein is such that the cellular levels of Bcl client proteins are reduced, and the amount of said chemotherapeutic agent is such that said Bcl client proteins are effectively inhibited by said chemotherapeutic agent.

In certain embodiments, the present invention relates to the aforementioned methods, wherein said compound is administered parenterally.

In certain embodiments, the present invention relates to the aforementioned methods, wherein said compound is administered intramuscularly, intravenously, subcutaneously, orally, pulmonary, intrathecally, topically or intranasally.

In certain embodiments, the present invention relates to the aforementioned methods, wherein said compound is administered systemically.

In certain embodiments, the present invention relates to the aforementioned methods, wherein said patient is a mammal.

In certain embodiments, the present invention relates to the aforementioned methods, wherein said patient is a primate.

In certain embodiments, the present invention relates to the aforementioned methods, wherein said patient is a human.

Pharmaceutical Compositions

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5)

sublingually; (6) ocularly; (7) transdermally; (8) nasally; (9) pulmonary; or (10) intrathecally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred per cent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrastemal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms. Preferred dosing is one administration per day.

While it is possible for a compound of the present invention to be administered alone, it is preferable to administer the compound as a pharmaceutical formulation (composition).

The compounds according to the invention may be formulated for administration in any convenient way for use in human or veterinary medicine, by analogy with other pharmaceuticals.

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W.H. Freedman and CO., San Francisco, U.S.A., 1969 or "Livestock Feeds and Feeding" O and B books, Corvallis, Oreg., U.S.A., 1977).

Micelles

Recently, the pharmaceutical industry introduced microemulsification technology to improve bioavailability of some lipophilic (water insoluble) pharmaceutical agents. Examples include Trimetrine (Dordunoo, S. K., et al., Drug Development and Industrial Pharmacy, 17(12), 1685-1713, 1991 and REV 5901 (Sheen, P. C., et al., J Pharm Sci 80(7), 712-714, 1991). Among other things, microemulsification provides enhanced bioavailability by preferentially directing absorption to the lymphatic system instead of the circulatory system, which thereby bypasses the liver, and prevents destruction of the compounds in the hepatobiliary circulation.

While all suitable amphiphilic carriers are contemplated, the presently preferred carriers are generally those that have Generally-Recognized-as-Safe (GRAS) status, and that can both solubilize the compound of the present invention and microemulsify it at a later stage when the solution comes into a contact with a complex water phase (such as one found in human gastro-intestinal tract). Usually, amphiphilic ingredients that satisfy these requirements have HLB (hydrophilic to lipophilic balance) values of 2-20, and their structures contain straight chain aliphatic radicals in the range of C-6 to C-20. Examples are polyethylene-glycolized fatty glycerides and polyethylene glycols.

Commercially available amphiphilic carriers are particularly contemplated, including Gelucire-series, Labrafil, Labrasol, or Lauroglycol (all manufactured and distributed by Gattefosse Corporation, Saint Priest, France), PEG-mono-oleate, PEG-di-oleate, PEG-mono-laurate and di-laurate, Lecithin, Polysorbate 80, etc (produced and distributed by a number of companies in USA and worldwide).

Polymers

Hydrophilic polymers suitable for use in the present invention are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. Preferred polymers are those having a molecular weight of from about 100 or 120 daltons up to about 5,000 or 10,000 daltons, and more preferably from about 300 daltons to about 5,000 daltons. In a particularly preferred embodiment, the polymer is polyethyleneglycol having a molecular weight of from about 100 to about 5,000 daltons, and more preferably having a molecular weight of from about 300 to about 5,000 daltons. In a particularly preferred embodiment, the polymer is polyethyleneglycol of 750 daltons (PEG(750)). Polymers may also be defined by the number of monomers therein; a preferred embodiment of the present invention utilizes polymers of at least about three monomers, such PEG polymers consisting of three monomers (approximately 150 daltons).

Other hydrophilic polymers which may be suitable for use in the present invention include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In certain embodiments, a formulation of the present invention comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

Cyclodextrins

Cyclodextrins are cyclic oligosaccharides, consisting of 6, 7 or 8 glucose units, designated by the Greek letter .alpha., .beta. or .gamma., respectively. Cyclodextrins with fewer than six glucose units are not known to exist. The glucose units are linked by alpha-1,4-glucosidic bonds. As a consequence of the chair conformation of the sugar units, all secondary hydroxyl groups (at C-2, C-3) are located on one side of the ring, while all the primary hydroxyl groups at C-6 are situated on the other side. As a result, the external faces are hydrophilic, making the cyclodextrins water-soluble. In contrast, the cavities of the cyclodextrins are hydrophobic, since they are lined by the hydrogen of atoms C-3 and C-5, and by ether-like oxygens. These matrices allow complexation with a variety of relatively hydrophobic compounds, including, for instance, steroid compounds such as 17.beta.-estradiol (see, e.g., van Uden et al. Plant Cell Tiss. Org. Cult. 38:1-3-113 (1994)). The complexation takes place by Van der Waals interactions and by hydrogen bond formation. For a general review of the chemistry of cyclodextrins, see, Wenz, Agnew. Chem. Int. Ed. Engl., 33:803-822 (1994).

The physico-chemical properties of the cyclodextrin derivatives depend strongly on the kind and the degree of substitution. For example, their solubility in water ranges from insoluble (e.g., triacetyl-beta-cyclodextrin) to 147% soluble (w/v) (G-2-beta-cyclodextrin). In addition, they are soluble in many organic solvents. The properties of the cyclodextrins enable the control over solubility of various formulation components by increasing or decreasing their solubility.

Numerous cyclodextrins and methods for their preparation have been described. For example, Parmeter (I), et al. (U.S. Pat. No. 3,453,259) and Gramera, et al. (U.S. Pat. No. 3,459,731) described electroneutral cyclodextrins. Other derivatives include cyclodextrins with cationic properties [Parmeter (II), U.S. Pat. No. 3,453,257], insoluble crosslinked cyclodextrins (Solms, U.S. Pat. No. 3,420,788), and cyclodextrins with anionic properties [Parmeter (III), U.S. Pat. No. 3,426,011]. Among the cyclodextrin derivatives with anionic properties, carboxylic acids, phosphorous acids, phosphinous acids, phosphonic acids, phosphoric acids, thiophosphonic acids, thiosulphinic acids, and sulfonic acids have been appended to the parent cyclodextrin [see, Parmeter (III), supra]. Furthermore, sulfoalkyl ether cyclodextrin derivatives have been described by Stella, et al. (U.S. Pat. No. 5,134,127).

Liposomes

Liposomes consist of at least one lipid bilayer membrane enclosing an aqueous internal compartment. Liposomes may be characterized by membrane type and by size. Small unilamellar vesicles (SUVs) have a single membrane and typically range between 0.02 and 0.05 µm in diameter; large unilamellar vesicles (LUVS) are typically larger than 0.05 µm Oligolamellar large vesicles and multilamellar vesicles have multiple, usually concentric, membrane layers and are typically larger than 0.1 µm. Liposomes with several nonconcentric membranes, i.e., several smaller vesicles contained within a larger vesicle, are termed multivesicular vesicles.

One aspect of the present invention relates to formulations comprising liposomes containing a compound of the present invention, where the liposome membrane is formulated to provide a liposome with increased carrying capacity. Alternatively or in addition, the compound of the present invention may be contained within, or adsorbed onto, the liposome bilayer of the liposome. The compound of the present invention may be aggregated with a lipid surfactant and carried within the liposome's internal space; in these cases, the liposome membrane is formulated to resist the disruptive effects of the active agent-surfactant aggregate.

According to one embodiment of the present invention, the lipid bilayer of a liposome contains lipids derivatized with polyethylene glycol (PEG), such that the PEG chains extend from the inner surface of the lipid bilayer into the interior space encapsulated by the liposome, and extend from the exterior of the lipid bilayer into the surrounding environment.

Active agents contained within liposomes of the present invention are in solubilized form. Aggregates of surfactant and active agent (such as emulsions or micelles containing the active agent of interest) may be entrapped within the interior space of liposomes according to the present invention. A surfactant acts to disperse and solubilize the active agent, and may be selected from any suitable aliphatic, cycloaliphatic or aromatic surfactant, including but not limited to biocompatible lysophosphatidylcholines (LPCs) of varying chain lengths (for example, from about $C_{14}$ to about $C_{20}$). Polymer-derivatized lipids such as PEG-lipids may also be utilized for micelle formation as they will act to inhibit micelle/membrane fusion, and as the addition of a polymer to surfactant molecules decreases the CMC of the surfactant and aids in micelle formation. Preferred are surfactants with CMCs in the micromolar range; higher CMC surfactants may be utilized to prepare micelles entrapped within liposomes of the present invention, however, micelle surfactant monomers could affect liposome bilayer stability and would be a factor in designing a liposome of a desired stability.

Liposomes according to the present invention may be prepared by any of a variety of techniques that are known in the art. See, e.g., U.S. Pat. No. 4,235,871; Published PCT applications WO 96/14057; New RRC, Liposomes: A practical approach, IRL Press, Oxford (1990), pages 33-104; Lasic D D, Liposomes from physics to applications, Elsevier Science Publishers BV, Amsterdam, 1993.

For example, liposomes of the present invention may be prepared by diffusing a lipid derivatized with a hydrophilic polymer into preformed liposomes, such as by exposing preformed liposomes to micelles composed of lipid-grafted polymers, at lipid concentrations corresponding to the final mole percent of derivatized lipid which is desired in the liposome. Liposomes containing a hydrophilic polymer can also be formed by homogenization, lipid-field hydration, or extrusion techniques, as are known in the art.

In one aspect of the present invention, the liposomes are prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323 (Apr. 12, 1988).

Release Modifiers

The release characteristics of a formulation of the present invention depend on the encapsulating material, the concentration of encapsulated drug, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. In all cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween® and Pluronic®. Pore forming agents which add microstructure to the matrices (i.e., water soluble compounds such as inorganic salts and sugars) are added as particulates. The range should be between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

EXEMPLIFICATION

The invention now being generally described, it will be more readily understood by reference to the following examples, which are included merely for purposes of illustration of certain aspects and embodiments of the present invention, and are not intended to limit the invention.

Example 1

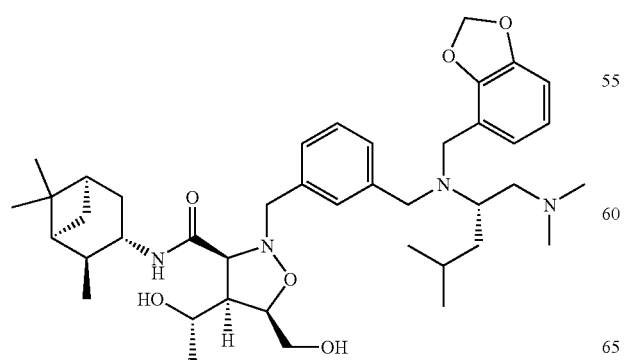

Part A

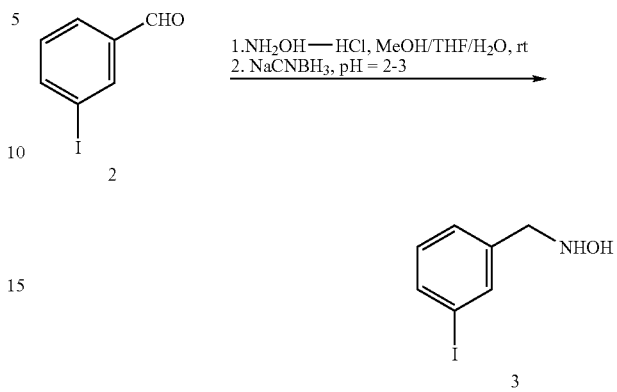

To a solution of 3-iodobenzaldehyde 2 (5.8 g, 25 mmol, 1 eq) in MeOH/THF (40 mL, 3:1) was added an aqueous solution of NH$_2$OH.HCl (2.04 g, 29.5 mmol, 1.2 eq, in 10 mL of water). The pH was adjusted to 9 using of 6 N KOH. The reaction was stirred at rt for 2 h and NaCNBH$_3$ (1.5 g, 25 mmol, 1 eq) was added followed by a crystal of methyl orange. The pH 2 was adjusted to 2 and the resulting ruby red color was maintained for the duration of the reaction by the addition of 1 N HCl. After 2 h, another portion of NaCNBH$_3$ (1.5 g, 25 mmol, 1 eq) was added. The mixture was stirred for 14 h, at which point, ⅔ of solvent was evaporated and the pH was raised to 9-10 by addition of a 6 N KOH aqueous solution. This mixture was extracted with DCM (3×100 mL). The organic layers were combined, washed with water then brine. The organic layer was dried over MgSO$_4$, filtered and evaporated in vacuo to afford 5.7 g of 3 as an off-white solid. 85% yield.

Part B

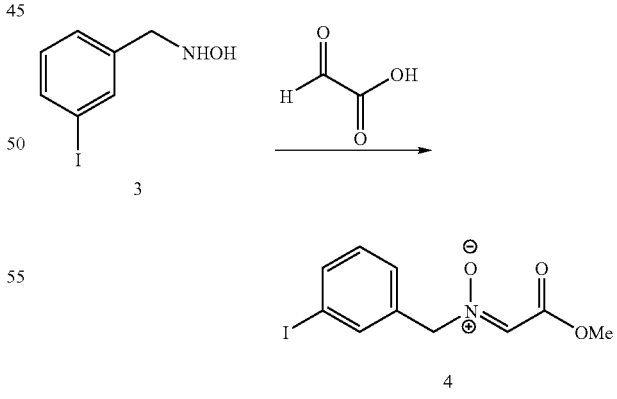

To a solution of N-(3-iodobenzyl)hydroxylamine 3 (16 g, 64 mmol, 1 eq) in benzene (320 mL) was added methyl glyoxylate (6.8 g, 80 mmol, 1.25 eq). The mixture was heated to 120° C. for 3 h using a Dean Stark trap. The solution was cooled to rt and the solvent was concentrated in vacuo to give 19.1 g of 4 as a yellow solid. 93% yield.

Part C

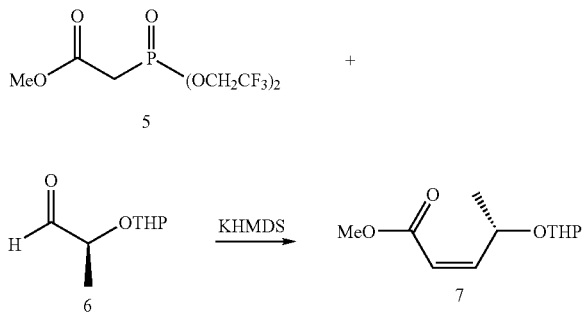

A solution of bis (2,2,2-trifluoroethyl)phosphonoacetic acid methyl ester 5 (28 g, 0.1 mmol, 1 eq) and 18-crown-6 (132 g, 0.50 mmol, 5 eq) in THF (2 L) was cooled to −78° C. under nitrogen. To the cooled solution was added potassium bis(trimethylsilyl)amide in toluene (20 g, 0.6 M in toluene 0.1 mmol, 1 eq). (S)-2-(tetrahydropyranyloxy) propanal 6 (synthesis described in *J. Chem. Soc., Perkin. Trans.* 1, 1994, 2791) (16 g, 0.1 mmol, 1 eq) was then added and the resulting mixture was stirred for 30 min at −78° C. A saturated aqueous NH$_4$Cl solution was then added and the product was extracted with ether (3×500 mL). The organic phases were combined, dried over Na$_2$SO$_4$, filtered and concentrated in vacuo. The crude material was purified via silica gel chromatography to afford 13.5 g of 13 an oil. 63% yield.

Part D

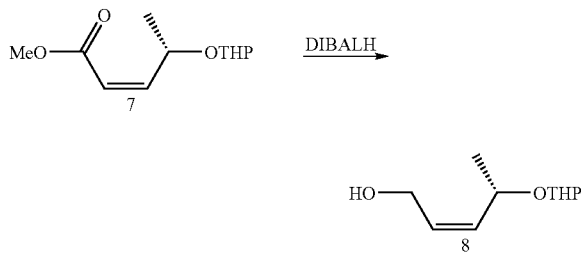

4(S)-(Tetrahydro-pyran-2-yloxy)-pent-2-enoic acid methyl ester 7 (10 g, 46.7 mmol, 1 eq) was reduced with DIBAL-H according to the procedure described in *J. Chem. Soc., Perkin. Trans.* 1, 1994, 2791 to afford 7.6 g of 8 4(S)-(Tetrahydro-pyran-2-yloxy)-pent-2-en-1-ol. 88% yield.

Part E

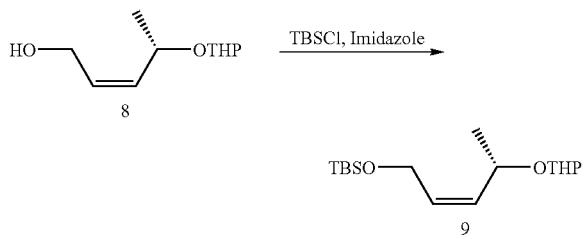

To a solution of 4(S)-(tetrahydro-pyran-2-yloxy)-pent-2-en-1-ol 8 (4.0 g, 22 mmol, 1 eq) in THF (20 mL) was added imidazole (3.66 g, 53.5 mmol, 2.4 eq) followed by TBSCl (3.89 g, 25.8 mmol, 1.2 eq). The reaction mixture was stirred at rt for 4 h, quenched with water (20 mL) and extracted with ether (3×10 mL). The combined organic extracts were washed with water (5×50 mL), brine (50 mL), dried over MgSO$_4$, filtered and concentrated in vacuo. The oil was purified by silica gel chromatography (30% Hexane/EtOAc) to afford 5.9 g of 9 as an oil. 92% yield.

Part F

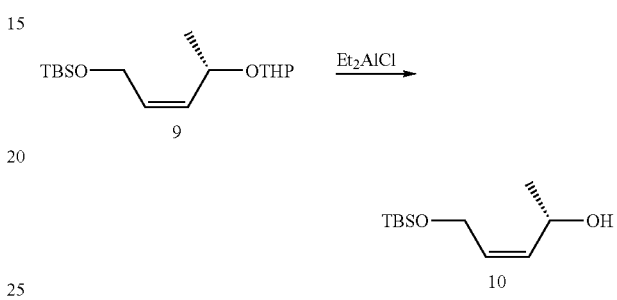

The THP protecting group was removed from t-butyl-dimethyl-[4(S)-(tetrahydro-pyran-2-yloxy)-pent-2-enyloxy]-silane 9 (10 g, 33 mmol, 1 eq) according to the procedure described in *Tetrahedron Letters* 1984, 25, 663 to afford 5.9 g of 10 as an oil. 83% yield.

Part G

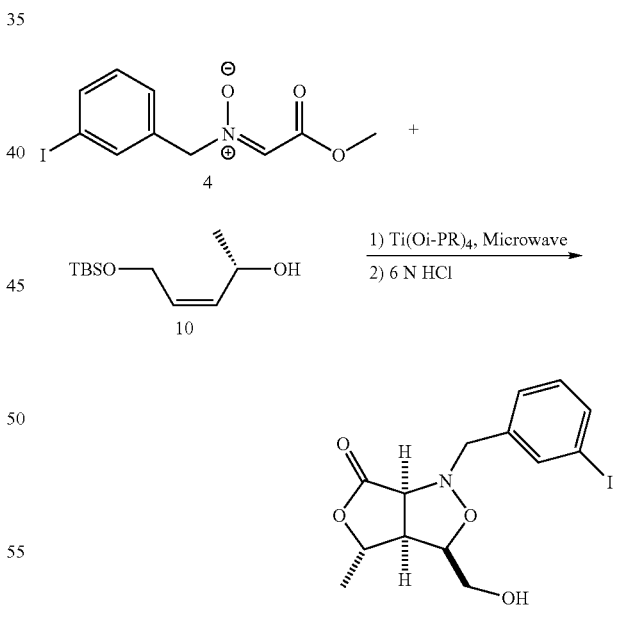

To a solution of nitrone methyl ester 4 (8.1 g, 38 mmol, 1 eq) and alcohol 10 (12 g, 38 mmol, 1 eq) in toluene (40 mL) was added Ti(OCH(CH$_3$)$_2$)$_4$ (16 g, 17 mL, 56 mmol, 1.5 eq). The suspension was heated in microwave oven to 140° C. for 30 min, and allowed to cool to rt. The solution was diluted with EtOAc (150 mL) and 3-(dimethylamino)-1,2-propanediol (7 g, 7 mL, 58 mmol, 1.5 eq) and stirred at rt for 8 h. To the solution was added water (100 mL), the organic phase was separated and the aqueous was washed with EtOAc (3×30 mL). The combined organic extracts were washed with water (100 mL), brine (100 mL), dried over $Na_2SO_4$, filtered and concentrated in vacuo. The crude material was purified by silica gel chromatography (1:29 $Et_2O$/DCM) to afford 13.5 g of 11 as a solid. 71% yield.

To a solution of the TBS protected isoxazolidine (13.5 g, 26 mmol, 1 eq) in THF (120 mL) was added 6 N HCl (67 mL). The solution was stirred at rt for 1.5 h, diluted water (25 mL) and extracted with EtOAc (3×80 mL), the organic extracts were combined and washed with saturated $NaHCO_3$ (50 mL), brine (50 mL), dried over $Na_2SO_4$ and concentrated in vacuo. The crude material was purified by silica gel chromatography (20-33% DCM/ether) to afford 9.5 g of 9 as a yellow solid. 64% overall yield for 2 steps.

Part H

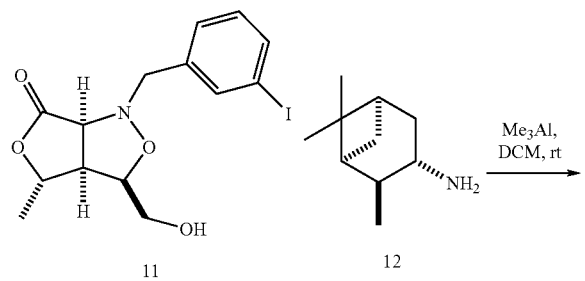

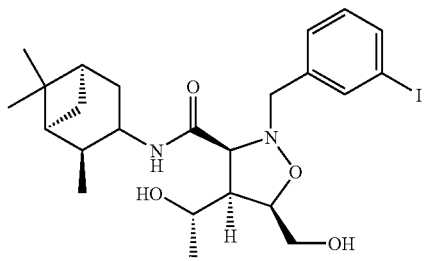

To a solution of (+) isopinocampheylamine 12 (0.2 g, 1.3 mmol, 6.5 eq) in DCM (10 mL) at rt was added $AlMe_3$ (0.85 mL of a 2 M solution in toluene, 1.7 mmol, 8.5 eq) dropwise over 2.5 min. The solution was stirred at rt for 10 min prior to the dropwise addition of a solution of lactone 11 (0.5 g, 0.02 mmol, 1 eq) in DCM (10 mL). The reaction was stirred for 1 h, diluted with DCM (125 mL) and a saturated aqueous solution of Rochelle's salt (125 mL). The mixture was vigorously stirred for 2 h until the two phases formed. The organic phase was separated, washed with water, brine, dried over $MgSO_4$, filtered and concentrated in vacuo to afford a solid. This material was used without further purification.

Part I

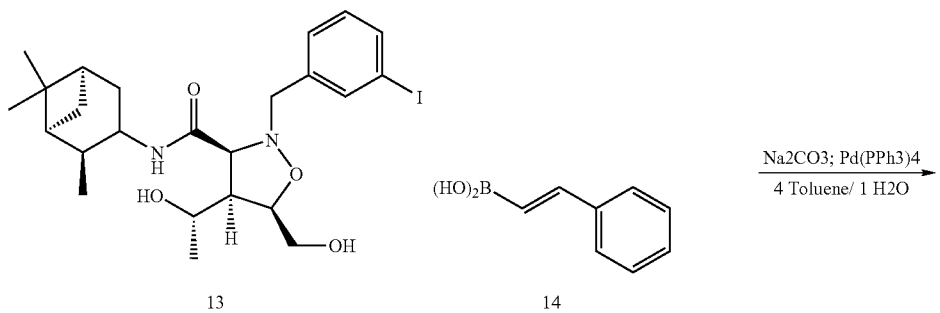

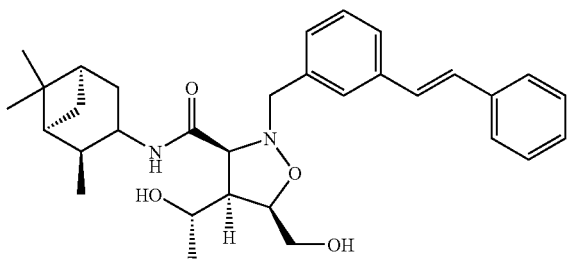

Aryl iodide 13 (1.44 g, 2.65 mmol, 1 eq), vinyl boronic acid 14 (1.57 g, 10.6 mmol, 10.0 eq), Na₂CO₃ (1.12 g, 10.6 mmol, 10.0 eq) and palladium tetrakis (0.61 g, 0.53 mmol, 0.2 eq) were weighed into a 100 ml flask. The flask was then purged with argon and content were dissolved in a 4:1 ratio of toluene/water (30 mL) and heated at 65° C. for 3 h. The organic layer was separated and the aqueous layer was extracted with EtOAc (3×20 mL). The organic layers were combined, washed with brine, dried over MgSO₄ and concentrated in vacuo. The crude material was purified by silica gel chromatography (solvent system) to afford 1.17 g of 15. 85% yield.

Part J

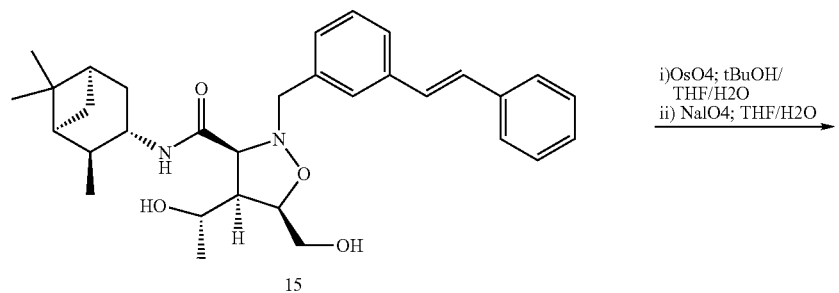
15

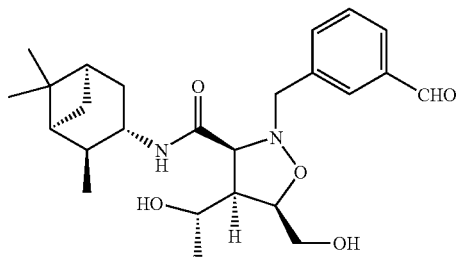
16

Part K

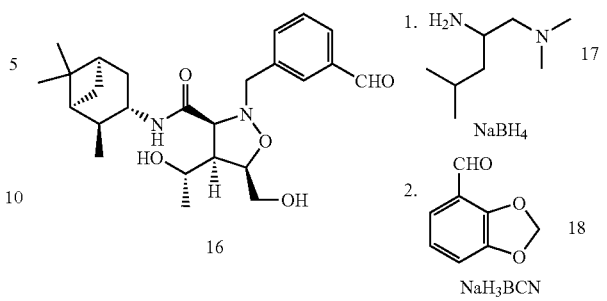

To a solution of 15 (0.11 g, 0.21 mmol, 1 eq) in tBuOH (16 ml), THF (8 ml), water (2 ml) was added NMO (0.11 g, 0.82 mmol, 4 eq) and a 2.5% solution of OsO₄ (2 mL, 0.21 g, 0.021 mmol, 1 eq) in tBuOH. After 4 h of stirring, the reaction was quenched with a solution of Na₂S₂O₃ and partitioned between EtOAc/brine. The aqueous layer was washed, dried organics over MgSO₄, filtered and concentrated in vacuo to give an oil.

The crude material (10 mg, 18 μmol, 1 eq) was then taken up in THF (0.2 mL), to which was added water (20 μL), and sodium periodate (4.1 mg, 19 μmol, 1.05 eq) and the reaction mixture was stirred overnight. The reaction was quenched with Na₂S₂O₃, washed with brine, dried over MgSO₄ and concentrated in vacuo. The crude material was purified by silica gel chromatography to afford 6.8 mg of 16 as a off white solid. 85% yield.

-continued

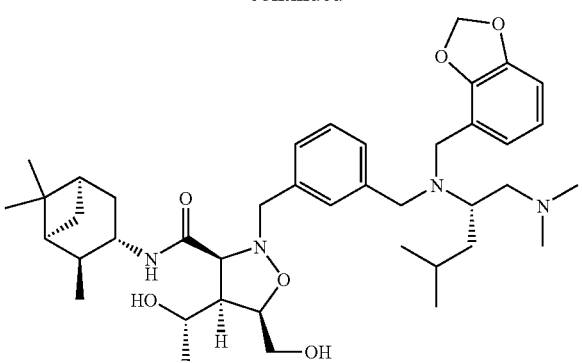
1

A solution of aldehyde 16 (40 mg, 90 μmol, 1 eq) in 1% aq. MeOH (2 mL) was treated with amine 17 (41 μL, 0.23 mmol, 2.6 eq.) and stirred for 1 h. NaBH$_4$ (4 mg, 90 μmol, 1 eq.) was added and the mixture was stirred during 0.5 h and the reaction was quenched with AcOH (10 uL).

Half of this crude reaction mixture was treated with 2,3-methylenedioxybenzaldehyde 18 (34 mg, 0.23 mmol, 5 eq.); after 0.25 h, NaBH$_3$CN (12 mg, 0.23 mmol, 5 eq.) was added and stirring continued overnight. The reaction mixture was purified directly by reverse-phase HPLC (CH$_3$CN/water with 40 mM NH$_4$HCO$_3$), to yield 20 mg of 1 as a white solid. 63% yield. MS (ESI(+)) m/z 707.76 (M+H)$^+$.

Example 2

Compound 19 was synthesized according to the procedure described in Example 1, using 3-ethoxysalicaldehyde in place of 2,3-methylenedioxybenzaldehyde. 34% yield. MS (ESI(+)) m/z 723.82 (M+H)$^+$.

Example 3

Compound 20 was synthesized according to the procedure described in Example 1, using 6-methoxysalicaldehyde in place of 2,3-methylenedioxybenzaldehyde. 29% yield. MS (ESI(+)) m/z 709.79 (M+H)$^+$.

Example 4

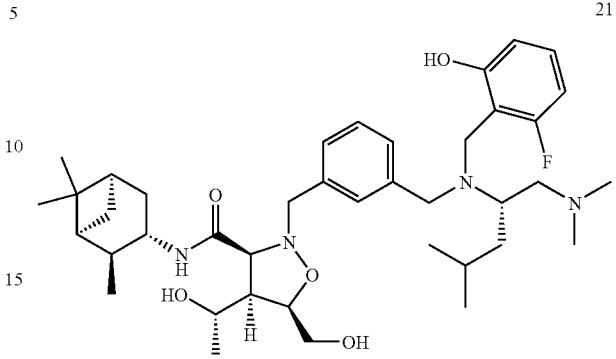

Compound 21 was synthesized according to the procedure described in Example 1, using 6-fluorosalicaldehyde in place of 2,3-methylenedioxybenzaldehyde. 38% yield. MS (ESI(+)) m/z 711.83 (M+H)$^+$.

Example 5

Compound 22 was synthesized according to the procedure described in Example 1, using 2-chlorobenzaldehyde in place of 2,3-methylenedioxybenzaldehyde. 35% yield.
MS (ESI(+)) m/z 740.68 (M+H)$^+$.

Example 6

Compound 23 was synthesized according to the procedure described in Example 1, using 2-allyloxybenzaldehyde in place of 2,3-methylenedioxybenzaldehyde. 50% yield. MS (ESI(+)) m/z 719.82 (M+H)⁺.

Example 7

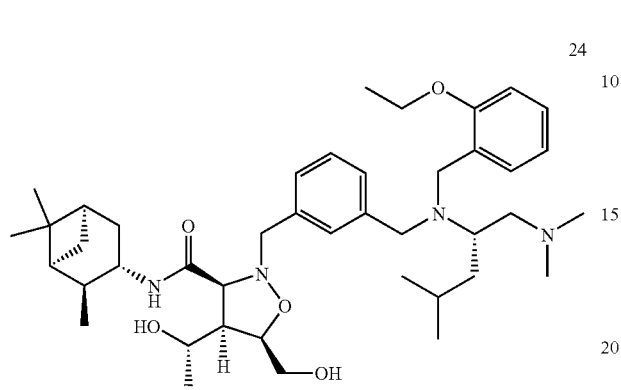

Compound 24 was synthesized according to the procedure described in Example 1, using 2-ethoxybenzaldehyde in place of 2,3-methylenedioxybenzaldehyde. 25% yield. MS (ESI(+)) m/z 707.82 (M+H)⁺.

Example 8

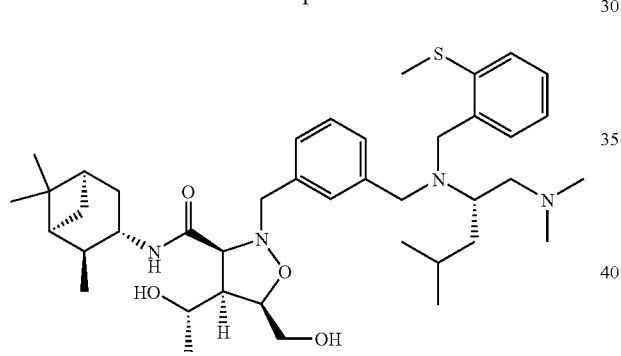

Compound 25 was synthesized according to the procedure described in Example 1, using 2-(methylthio)benzaldehyde in place of 2,3-methylenedioxybenzaldehyde. 38% yield. MS (ESI(+)) m/z 709.72 (M+H)⁺.

Example 9

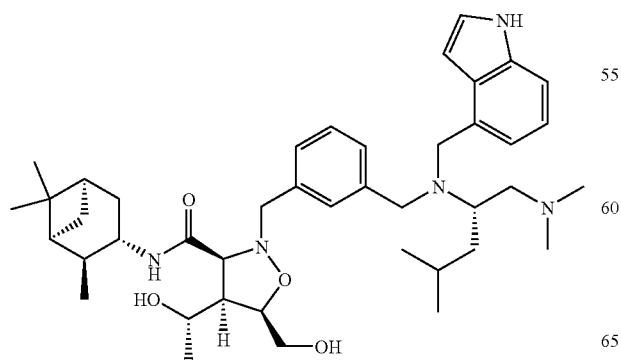

Compound 26 was synthesized according to the procedure described in Example 1, using 4-formylindole in place of 2,3-methylenedioxybenzaldehyde. 25% yield. MS (ESI(+)) m/z 702.80 (M+H)⁺.

Example 10

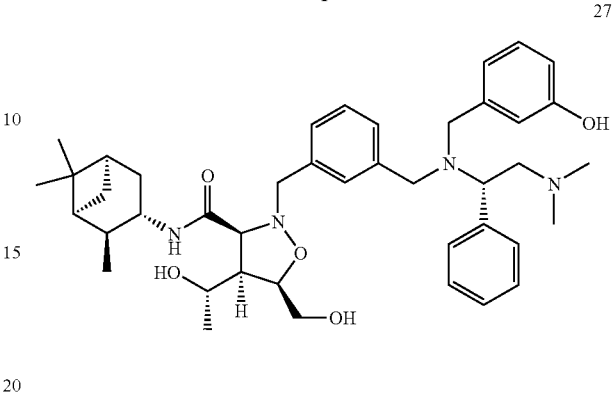

Compound 27 was synthesized according to the procedure described in Example 1, using 3-hydroxybenzaldehyde in place of 2,3-methylenedioxybenzaldehyde and (S)—N$^1$,N$^1$-dimethyl-2-phenylethane-1,2-diamine in place of amine 17. 45% yield. MS (ESI(+)) m/z 666.89 (M+H)⁺.

Example 11

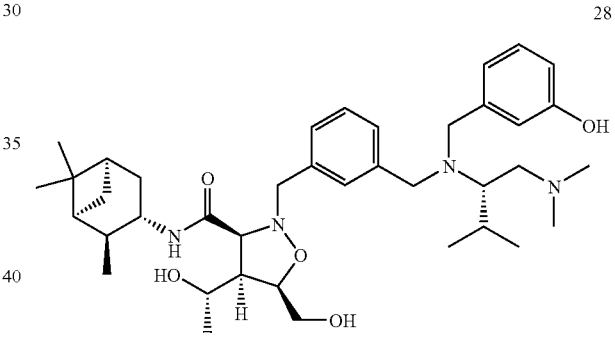

Compound 28 was synthesized according to the procedure described in Example 1, using 3-hydroxybenzaldehyde in place of 2,3-methylenedioxybenzaldehyde and (S)—N$^1$,N$^1$,3-trimethylbutane-1,2-diamine in place of amine 17. 47% yield. MS (ESI(+)) m/z 665.85 (M+H)⁺.

Example 12

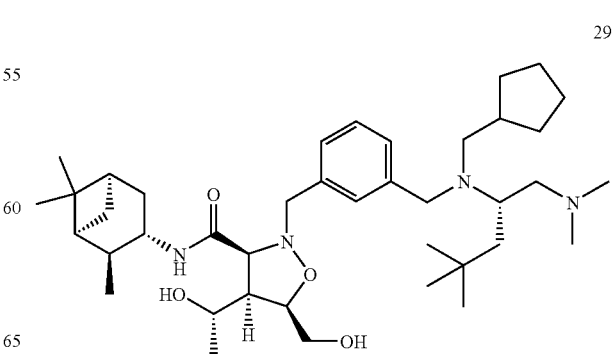

Compound 29 was synthesized according to the procedure described in Example 1, using cyclopentanecarboxaldehyde in place of 2,3-methylenedioxybenzaldehyde and (S)—N$^1$,N$^1$,4,4-tetramethylpentane-1,2-diamine in place of amine 17. 37% yield. MS (ESI(+)) m/z 669.91 (M+H)$^+$.

Example 13

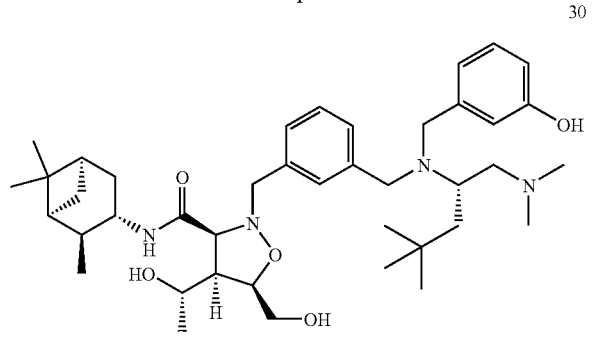

Compound 30 was synthesized according to the procedure described in Example 1, using 3-hydroxybenzaldehyde in place of 2,3-methylenedioxybenzaldehyde and amine (S)—N$^1$,N$^1$,4,4-tetramethylpentane-1,2-diamine in place of amine 17. 48% yield. MS (ESI(+)) m/z 693.92 (M+H)$^+$.

Example 14

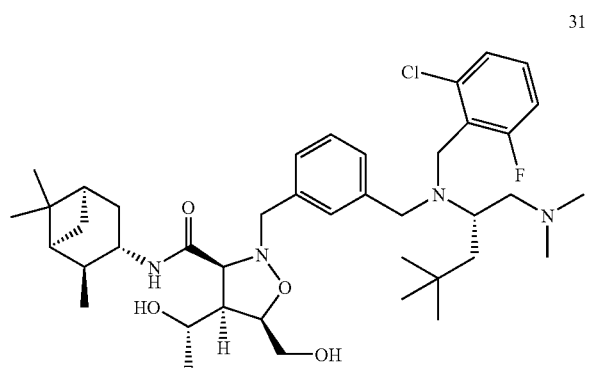

Compound 31 was synthesized according to the procedure described in Example 1, using 2-chloro-6-fluorobenzaldhyde in place of 2,3-methylenedioxybenzaldehyde and (S)—N$^1$,N$^1$,4,4-tetramethylpentane-1,2-diamine in place of amine 17. 52% yield. MS (ESI(+)) m/z 729.86 (M+H)$^+$.

Example 15

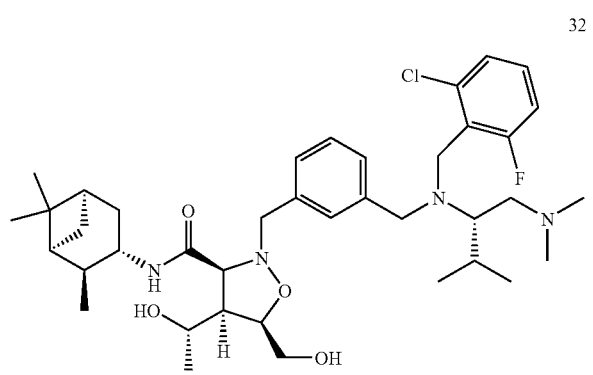

Compound 32 was synthesized according to the procedure described in Example 1, using 2-chloro-6-fluorobenzaldhyde in place of 2,3-methylenedioxybenzaldehyde and (S)—N$^1$,N$^1$,3-trimethylbutane-1,2-diamine in place of amine 17. 35% yield. MS (ESI(+)) m/z 701.79 (M+H)$^+$.

Example 16

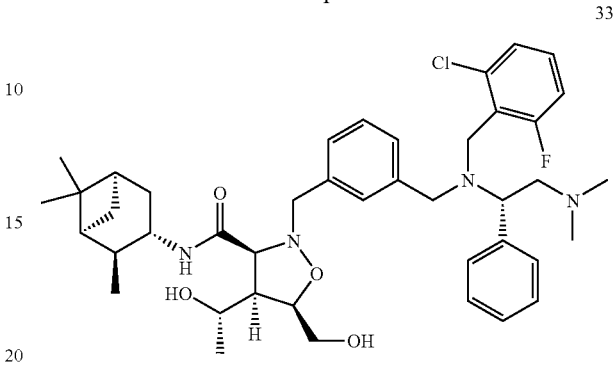

Compound 44 was synthesized according to the procedure described in Example 1, using 2-chloro-6-fluorobenzaldhyde in place of 2,3-methylenedioxybenzaldehyde and (S)—N$^1$,N$^1$-dimethyl-2-phenylethane-1,2-diamine in place of amine 17. 21% yield. MS (ESI(+)) m/z 735.83 (M+H)$^+$.

Example 17

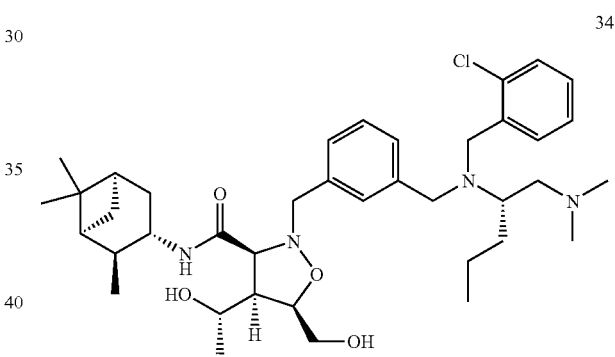

Compound 34 was synthesized according to the procedure described in Example 1, using 2-chlorobenzaldhyde in place of 2,3-methylenedioxybenzaldehyde and (S)—N$^1$,N$^1$-dimethylpentane-1,2-diamine in place of amine 17. 53% yield. MS (ESI(+)) m/z 683.75 (M+H)$^+$.

Example 18

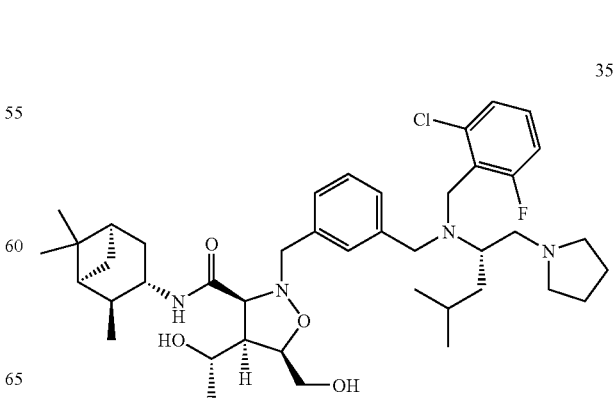

Compound 35 was synthesized according to the procedure described in Example 1, using 2-chloro-6-fluorobenzaldhyde in place of 2,3-methylenedioxybenzaldehyde and (S)-1-(1-pyrrolidinyl)-2-amino-4-methyl-pentane in place of amine 17. 30% yield. MS (ESI(+)) m/z 741.86 (M+H)+.

Example 19

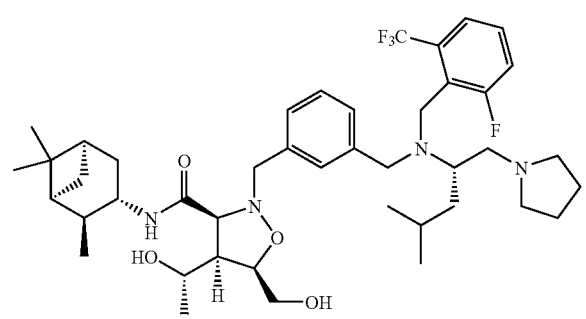

36

Compound 36 was synthesized according to the procedure described in Example 1, using 2-trifluoromethyl-6-fluorobenzaldhyde in place of 2,3-methylenedioxybenzaldehyde and (S)-1-(1-pyrrolidinyl)-2-amino-4-methyl-pentane in place of amine 17. 23% yield. MS (ESI(+)) m/z 775.90 (M+H)+.

Example 20

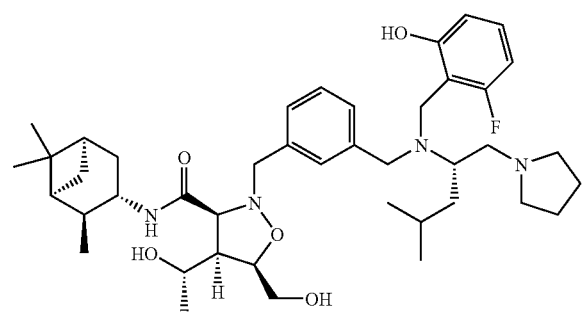

37

Compound 37 was synthesized according to the procedure described in Example 1, using 6-fluorosalicaldhyde in place of 2,3-methylenedioxybenzaldehyde and (S)-1-(1-pyrrolidinyl)-2-amino-4-methyl-pentane in place of amine 17. 31% yield. MS (ESI(+)) m/z 723.89 (M+H)+.

Example 21

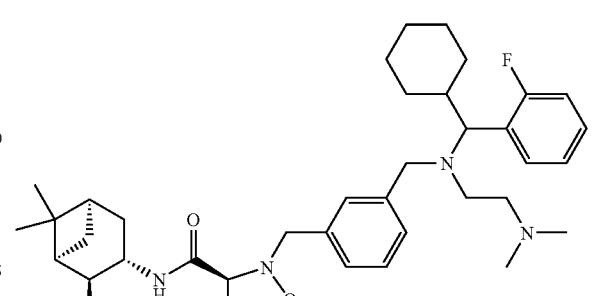

38

Part A

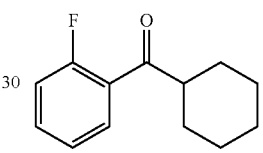

39

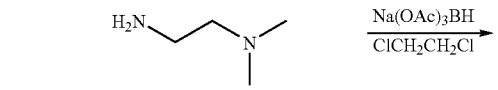

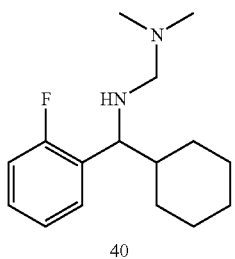

40

To a solution of ketone 39 (500 mg, 2.42 mmol, 1 eq) in DCE (5 mL) was added $N^1,N^1$-dimethylethane-1,2-diamine (641 mg, 7.27 mmol, 3 eq) followed by Na(OAc)$_3$BH (771 mg, 3.64 mmol, 1.5 eq) and the reaction was heated to 40° C. After stirring for 48 h, the reaction mixture was diluted with water (100 mL), EtOAc (100 mL), brine (100 mL) and the pH was adjusted to 12 with 6 N NaOH. The mixture was extracted with EtOAc (2×100 mL) and the combined organics were dried over MgSO$_4$, filtered and concentrated in vacuo to afford 200 mg of diamine 40 as a dark brown oil. The crude oil was used directly without further purification.

Part B

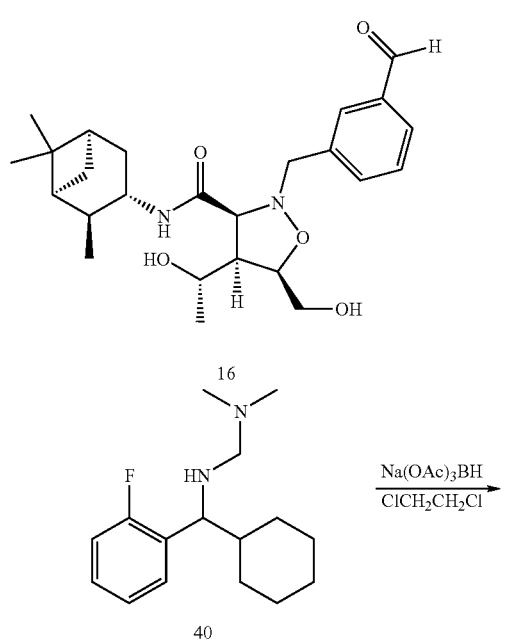

16

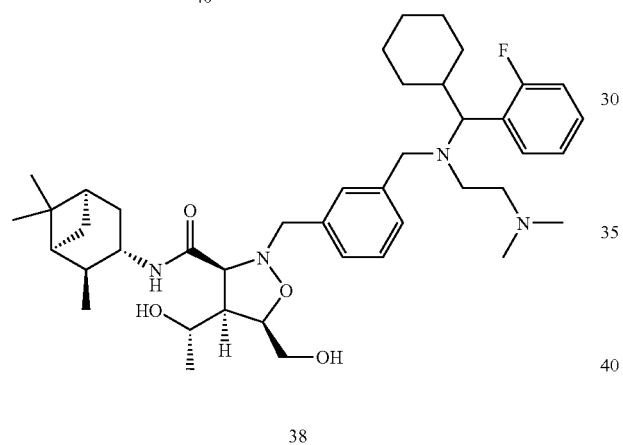

38

To a solution of aldehyde 16 (30 mg, 0.07 mmol) in DCE (1 mL) was added diamine 40 (0.02 mg, 0.07 mmol) followed by Na(OAc)₃BH (20 mg, 0.1 mmol) and the reaction was heated to a 40° C. After stirring for 48 h, an additional portion of aldehyde (30 mg, 0.02 mmol) and Na(OAc)₃BH (20 mg, 0.1 mmol) was added and the reaction was stirred at 40° C. After 24 h, the reaction mixture was purified directly by reverse-phase HPLC (CH₃CN/water with 40 mM NH₄HCO₃) to yield 20 mg of 38. Yield 42%. MS (ESI(+)) m/z 707.5. (M+H)⁺.

Example 22

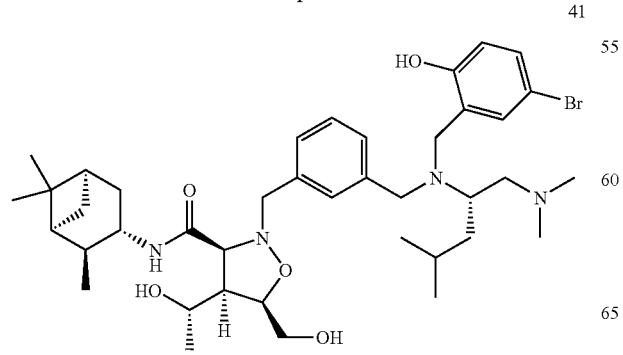

41

Compound 41 was synthesized according to the procedure described in Example 1, using 2-bromo-5-(hydroxyl)benzaldehyde in place of 2,3-methylenedioxybenzaldehyde. Yield 38%. MS (ESI(+)) m/z 757.6 (M+H)⁺.

Example 23

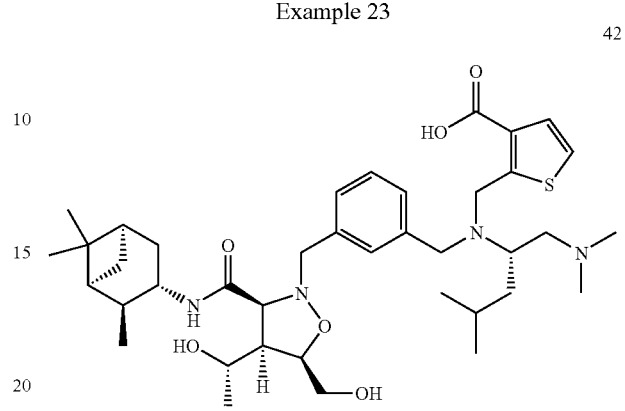

42

Compound 42 was synthesized according to the procedure described in Example 1, using 2-formylthiophene-2-carboxylic acid in place of 2,3 methylenedioxybenzaldehyde. Yield 48%. MS (ESI(+)) m/z 713.8 (M+H)⁺.

Example 24

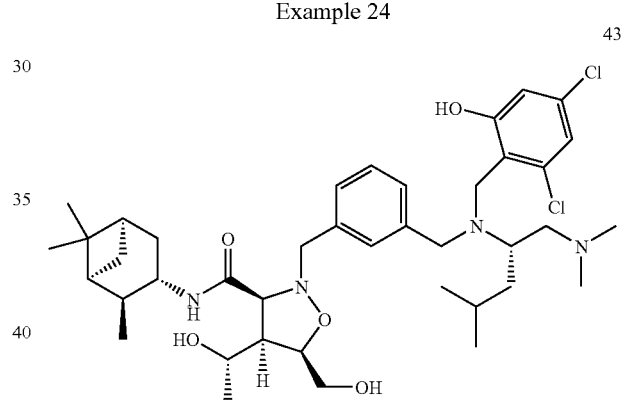

43

Compound 43 was synthesized according to the procedure described in Example 1, using 2,4-dichloro-6-hydroxylbenzaldehyde in place of 2,3 methylenedioxybenzaldehyde. Yield 27%. MS (ESI(+)) m/z 747.8 (M+H)⁺.

Example 25

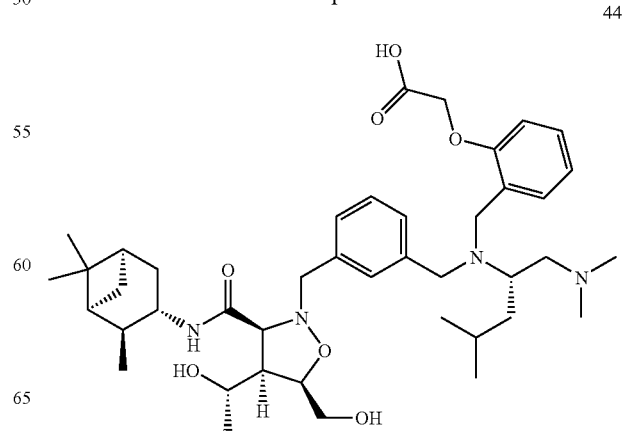

44

Compound 44 was synthesized according to the procedure described in Example 1, using 2-formylphenoxyacetic acid in place of 2,3 methylenedioxybenzaldehyde. Yield 47%. MS (ESI(+)) m/z 737.7 (M+H)+.

Example 26

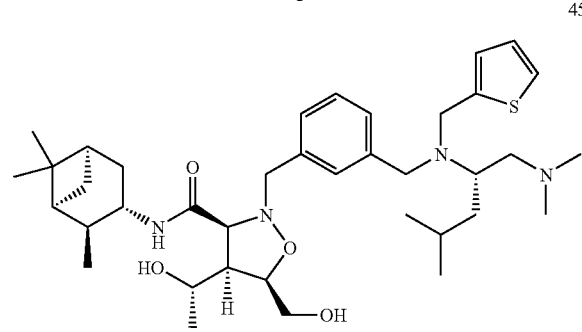

Compound 45 was synthesized according to the procedure described in Example 1, using thiophene-2-carboxaldehyde in place of 2,3 methylenedioxybenzaldehyde. Yield 69%. MS (ESI(+)) m/z 669.8 (M+H)+.

Example 27

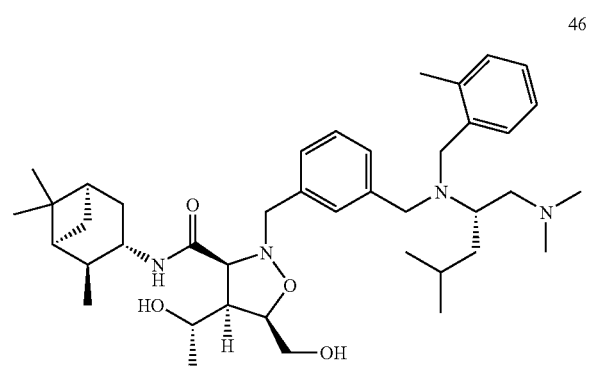

Compound 46 was synthesized according to the procedure described in Example 1, using o-tolualdehyde in place of 2,3 methylenedioxybenzaldehyde. Yield 51%. MS (ESI(+)) m/z 677.9 (M+H)+.

Example 28

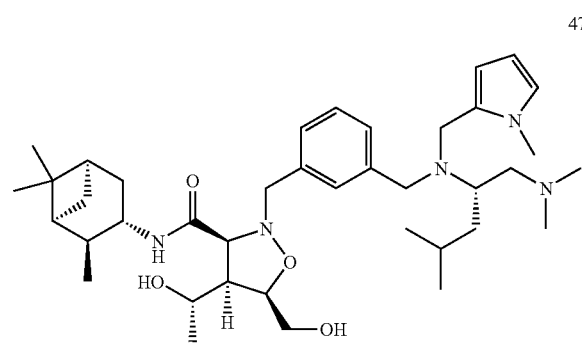

Compound 47 was synthesized according to the procedure described in Example 1, using 1-methylpyrrole-2-carbox aldehyde in place of 2,3 methylenedioxybenzaldehyde. Yield 43%. MS (ESI(+)) m/z 666.9 (M+H)+.

Example 29

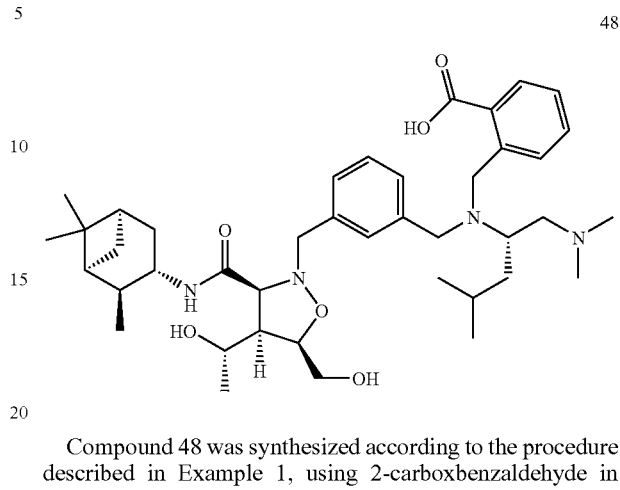

Compound 48 was synthesized according to the procedure described in Example 1, using 2-carboxbenzaldehyde in place of 2,3 methylenedioxybenzaldehyde. Yield 65%. MS (ESI(+)) m/z 707.9 (M+H)+.

Example 30

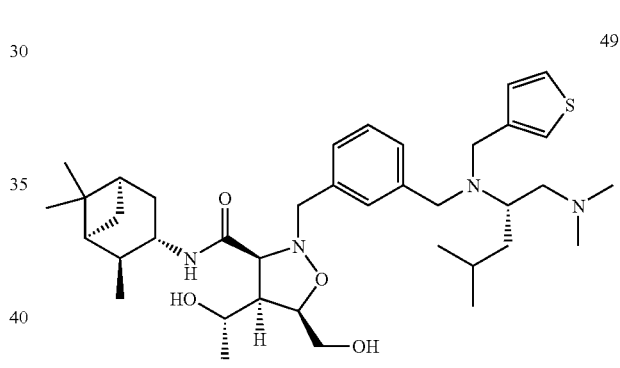

Compound 49 was synthesized according to the procedure described in Example 1, using thiophene-3-carboxaldehyde in place of 2,3-methylenedioxybenzaldehyde. Yield 69%. MS (ESI(+)) m/z 669.8 (M+H)+.

Example 31

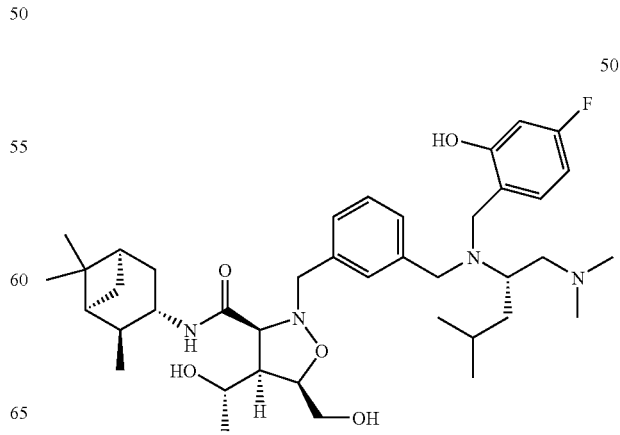

Compound 50 was synthesized according to the procedure described in Example 1, using 4-fluoro-2-hydroxbenzaldehyde in place of 2,3 methylenedioxybenzaldehyde. Yield 15%. MS (ESI(+)) m/z 697.8 (M+H)+.

Example 32

51
Part A

52

Part B

53

To a solution of Boc-L-Leucine 53 (5 g, 22 mmol, 1 eq) and PyBop (15 g, 28 mmol, 1.3) in DCM (60 mL) was added pyrrolidine at 0° C. The solution was stirred for 10 min followed by dropwise addition of DIPEA (6 g, 8 mL, 48 mmol, 2.2 eq). After stirring for 6 h, the solution was diluted with sat NaHCO₃ (40 mL) and the aqueous phase was extracted with DCM (2×50 mL). The combined organic phases were washed with brine, separated, dried over MgSO₄, filtered and concentrated in vacuo to afford an oil. The resulting oil was purified by silica gel chromatography (50-100% hexane/EtOAc) to afford 53 as a clear oil.

53

54

To a solution of amide 53 (4.5 g, 15.8 mmol, 1 eq) in DCM (100 mL) was added TFA (10 mL) at 0° C. After stirring for 2 h at rt, the solvent was removed in vacuo to afford an oil. The resulting oil was suspended in THF and cooled to 0° C., to which was added LiAlH₄ (4 g, 108 mmol, 6.8 eq) in portions, and heated at reflux for 12 h under argon. The solution was cooled to rt and quenched with water (4 mL), allowed to stir for 5 min, followed by 15% NaOH (4 mL) and stirred for additional 5 min, and finally water (12 mL) was added and the suspension was stirred until the white precipitate formed. The solid was filtered and washed with EtOAc and the filtrate was concentrated in vacuo to afford 54 as an oil which was used without further purification.

Part C

16

54

55

To a solution of 16 (250 mg, 0.56 mmol, 1 eq) in MeOH (25 mL) was added 54 (96 mg, 0.56 mmol, 1 eq) and stirred at rt for 3 h, followed by the addition of NaBH₄ (21 mg, 0.56 mmol, 1 eq). After stirring at rt for 12 h the reaction mixture was diluted with AcOH (0.08 mL) and concentrated in vacuo to afford an oil which was used with further purification.

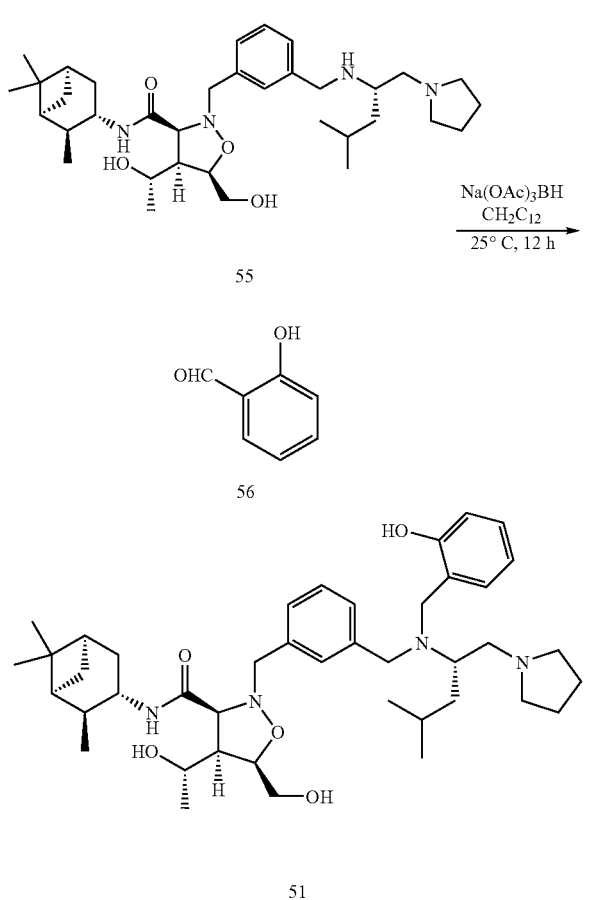

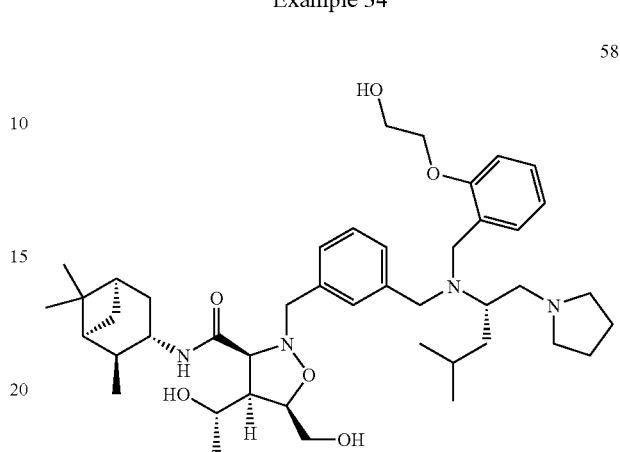

To a solution of 55 (15 mg, 25 μmol, 1 eq) in DCM (1.0 mL) was added 2-hydroxbenzaldehyde (5 mg, 38 μmol, 1.5 eq) followed by the addition of Na(OAc)₃BH (11 mg, 50 μmol, 2 eq). After stirring at rt for 12 h the reaction mixture was diluted with AcOH (0.1 mL) and stirred for 10 min. The reaction mixture was diluted with DCM (2.5 mL) and washed with sat. NaHCO₃ (2.5 mL), organic phase was separated, dried over Na₂SO₄ and concentrated in vacuo to afford an oil. The oil was purified directly by reverse-phase HPLC (CH₃CN/water with 40 mM NH₄HCO₃) to 7 mg of give 51 as a white solid. Yield 40%. MS (ESI(+)) m/z 705.9 (M+H)⁺.

Example 33

Compound 57 was synthesized according to the procedure described in example 32, using 2-formylbenzenesulfonic acid in place of 2-hydroxybenzaldehyde. Yield 39%. MS (ESI(+)) m/z 705.9 (M+H)⁺.

Example 34

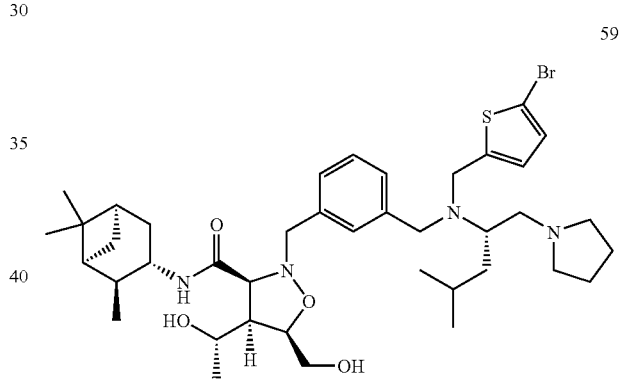

Compound 58 was synthesized according to the procedure described in example 32, using 2-(2-hydroxyethoxy)benzaldehyde in place of 2-hydroxybenzaldehyde. Yield 32%. MS (ESI(+)) m/z 749.9 (M+H)⁺.

Example 35

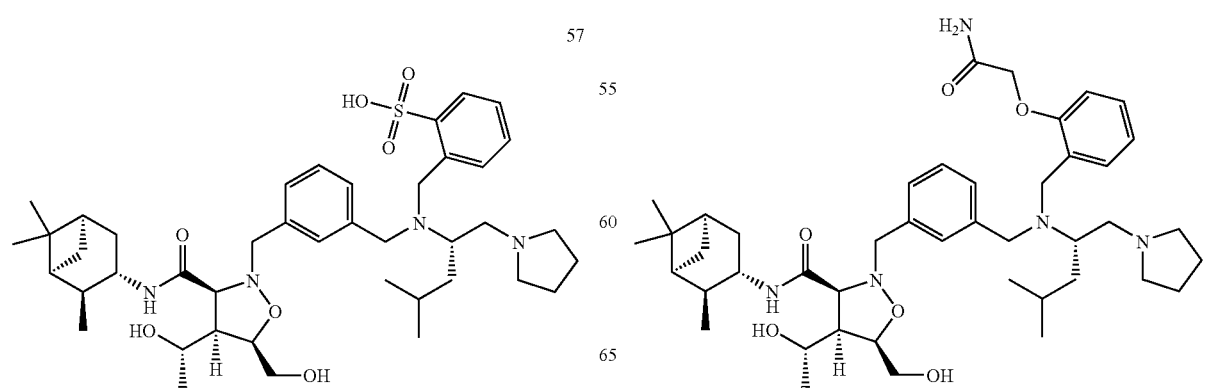

Compound 59 was synthesized according to the procedure described in example 32, using 5-bromothiophene-2-carboxaldehyde in place of 2-hydroxybenzaldehyde. Yield 54%. MS (ESI(+)) m/z 775.7 (M+H)⁺.

Example 36

Compound 60 was synthesized according to the procedure described in example 32, using 2-(2-formyl-phenoxy)-acetamide in place of 2-hydroxybenzaldehyde. Yield 35%. MS (ESI(+)) m/z 762.9 (M+H)+.

Example 37

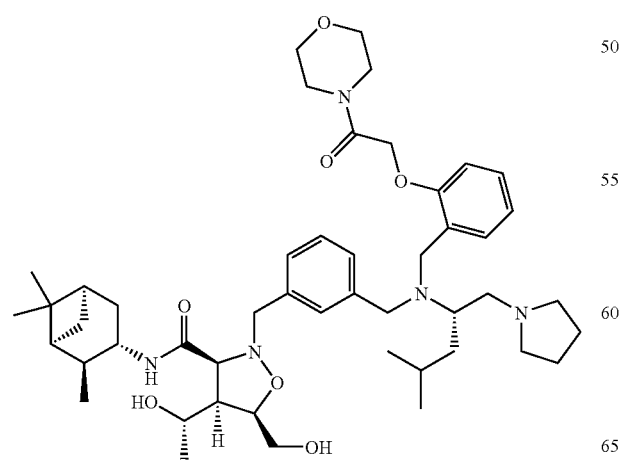

61

Compound 61 was synthesized according to the procedure described in example 32, using 2-formylphenxyacetic acid in place of 2-hydroxybenzaldehyde. Yield 59%. MS (ESI(+)) m/z 775.7 (M+H)+.

Example 38

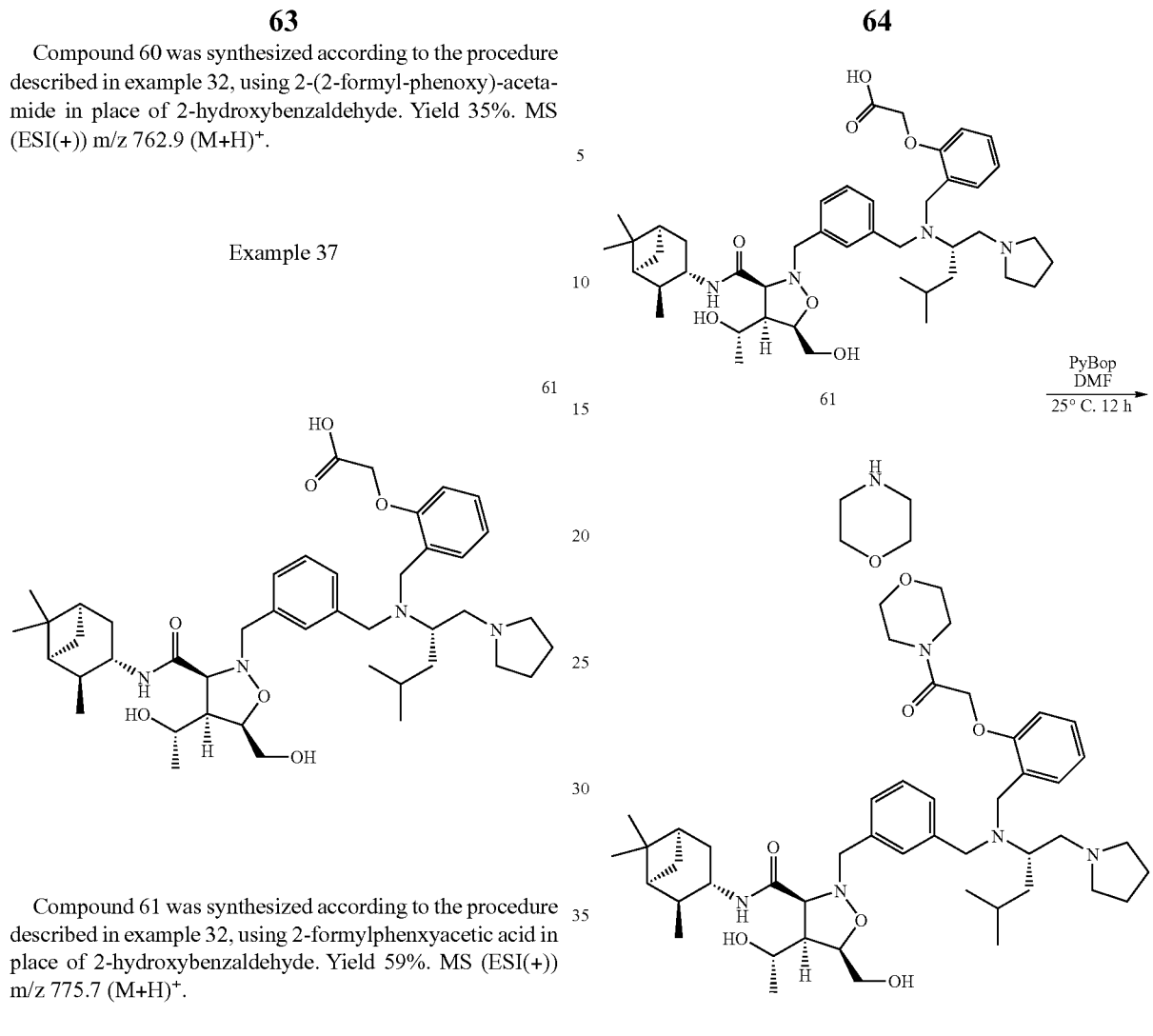

62

To a solution of 61 (10 mg, 10 μmol, 1 eq) in DMF (0.5 mL) was added PyBop (10 mg, 20 μmol, 2 eq), morpholine (2 mg, 30 μmol, 3 eq) and Et₃N (4 mg, 5 uL, 40 μmol, 4 eq). The solution was stirred for 12 h, diluted with water (0.5 mL) and the reaction mixture was purified directly by reverse-phase HPLC (CH₃CN/water with 40 mM NH₄HCO₃) to give 3 mg of 62 as a white solid. Yield 28%. MS (ESI(+)) m/z 833 (M+H)+.

Example 39

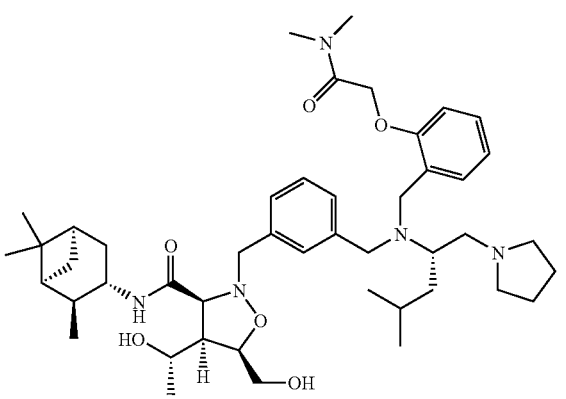

63

Compound 63 was synthesized according to the procedure described in example 38, using dimethylamine in place of morpholine. Yield 59%. MS (ESI(+)) m/z 775.7 (M+H)+.

Example 40

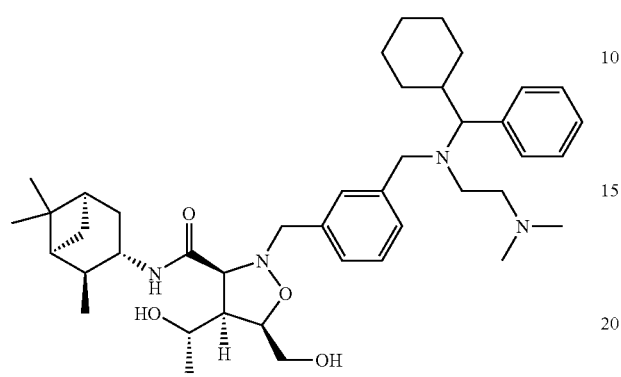

Compound 64 was synthesized according to the procedure described in example 21, using cyclohexyl(phenyl)methanone in place of cyclohexyl(2-fluorophenyl)methanone. Yield 29%. MS (ESI(+)) m/z 689.49 (M+H)+.

Example 41

Bcl-2 binding affinity data is presented below for various compounds of the invention. As tabulated below, "**" indicates that the Ki is <1 nM; "*" indicates that the Ki is 1-5 nM; "**" indicates that the Ki is 5-9 nM; and "*" indicates that the Ki is >9 nM.

Bcl-xL binding affinity data is presented below for various compounds of the invention. As tabulated below, "†††" indicates that the Ki is <0.2 µM; "††" indicates that the Ki is 0.2-1 µM; and "†" indicates that the Ki is >1 µM.

| Bcl-2 Activity | Symbol |
|---|---|
| <1 nM | **** |
| 1-5 nM | *** |
| 5-9 nM | ** |
| >9 nM | * |

| Bcl-XL Activity | Symbol |
|---|---|
| <0.2 uM | ††† |
| 0.2-1 uM | †† |
| >1 uM | † |

| Compound | Bcl-2 | Bcl-XL |
|---|---|---|
| 1 | *** | †† |
| 19 | *** | †† |
| 20 | ** | †† |
| 21 | * | †† |
| 22 | * | ††† |
| 23 | *** | †† |
| 24 | *** | †† |
| 25 | *** | †† |
| 26 | * | †† |
| 27 | ** | ††† |
| 28 | ** | †† |
| 29 | **** | †† |
| 30 | *** | ††† |
| 31 | **** | ††† |
| 32 | *** | ††† |
| 33 | *** | ††† |
| 34 | ** | ††† |
| 35 | *** | ††† |
| 36 | ** | ††† |
| 37 | *** | ††† |
| 38 | *** | †† |
| 41 | ** | ††† |
| 42 | *** | ††† |
| 43 | * | ††† |
| 44 | ** | ††† |
| 45 | *** | ††† |
| 46 | *** | ††† |
| 47 | *** | ††† |
| 48 | *** | †† |
| 49 | *** | †† |
| 50 | *** | †† |
| 51 | *** | ††† |
| 57 | ** | †† |
| 58 | * | †† |
| 59 | *** | ††† |
| 60 | *** | ††† |
| 62 | *** | ††† |
| 63 | *** | ††† |
| 64 | *** | † |

Incorporation by Reference

All of the U.S. patents and U.S. patent application publications cited herein are hereby incorporated by reference.

Equivalents

Those skilled in the art will recognize, or be able to ascertain using no more than routine experimentation, many equivalents to the specific embodiments of the invention described herein. Such equivalents are to be encompassed by the following claims.

We claim:
1. A compound of formula 1:

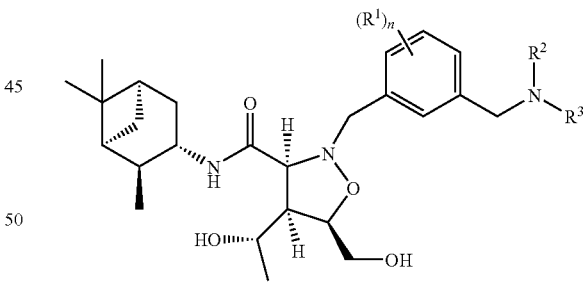

or a pharmaceutically acceptable salt thereof;
wherein independently for each occurrence;
n is 0, 1, 2, 3, or 4;
$R^1$ independently for each occurrence is H, alkyl, alkenyl, alkynyl, aryl, aralkyl, heterocyclyl, heterocyclylalkyl, heteroaryl, heteroaralky, halide, hydroxyl, alkoxyl, aryloxy, acyloxy, amino, alkylamino, arylamino, acylamino, aralkylamino, nitro, acylthio, carboxamide, carboxyl, nitrile, —$COR^5$, —$CO_2R^5$, —$N(R^5)CO_2R^6$, —$OC(O)N(R^5)(R^6)$, —$N(R^5)SO_2R^6$, or —$N(R^5)C(O)N(R^5)(R^6)$;
$R^2$ and $R^3$ independently for each occurrence are H, alkyl, alkenyl, alkynyl, aryl, aralkyl, heterocyclyl, heterocyclylalkyl, heteroaryl, heteroaralkyl, or —[C(R⁵)(R⁶)]$_p$—R⁴; or has the formula 1a

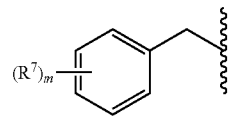

wherein m is 0, 1, 2, 3, 4, or 5;

R⁷ for each occurrence independently is H, alkyl, aryl, alkenyl, halide, hydroxyl, alkoxyl, alkenyloxy, aryloxy, acyloxy, amino, alkylamino, arylamino, acylamino, aralkylamino, nitro, acylthio, carboxamide, carboxyl, nitrile, —OSO₃R⁵, —SO₂R⁵, —S(O)R⁵, —SR⁵, —PO₂OR⁵, —OPO₂OR⁵, —COR⁵, —CO₂R⁵, —OCH₂CO₂R⁵, or —OCH₂C(O)N(R⁵)(R⁶); or two occurrences of R⁷ taken together may form a monocyclic ring between 5-8 ring atoms, of which, one, two, or three atoms are independently S, O, or N;

R⁴ is halide, hydroxyl, alkoxyl, aryloxy, acyloxy, amino, alkylamino, arylamino, acylamino, aralkylamino, nitro, acylthio, carboxamide, carboxyl, nitrile, —OSO₃R⁵, —SO₂R⁵, —S(O)R⁵, —PO₂OR⁵, —OPO₂OR⁵, —COR⁵, —CO₂R⁵, —N(R⁵)CO₂R⁶, —OC(O)N(R⁵)(R⁶), —N(R⁵)SO₂R⁶, or —N(R⁵)C(O)N(R⁵)(R⁶); and each of R⁵ and R⁶ independently for each occurrence is H, alkyl, alkenyl, alkynyl, aryl, aralkyl, cycloalkyl, heterocyclyl, heterocyclylalkyl, heteroaryl, or heteroaralkyl; or R⁵ and R⁶ taken together form a monocyclic ring with 4-8 ring atoms, of which one, two, or three ring atoms are independently S, O, or N.

2. A compound selected from the group consisting of:

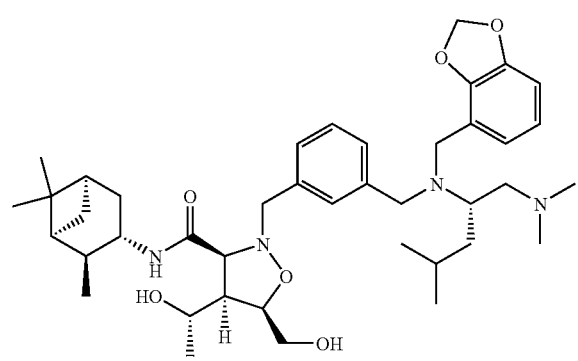

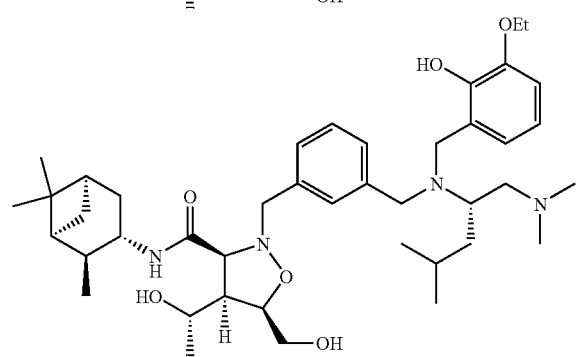

-continued

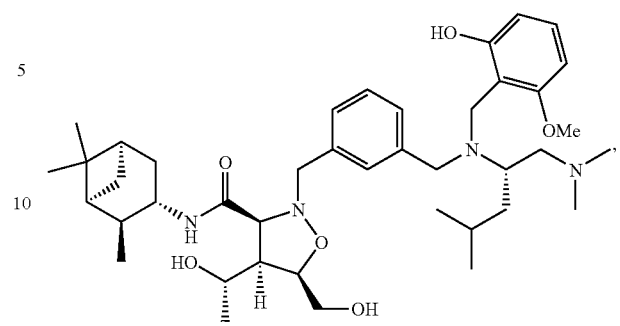

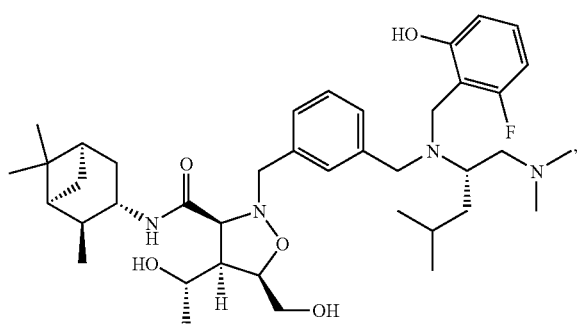

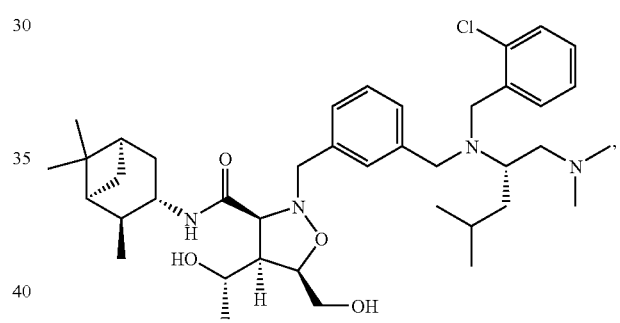

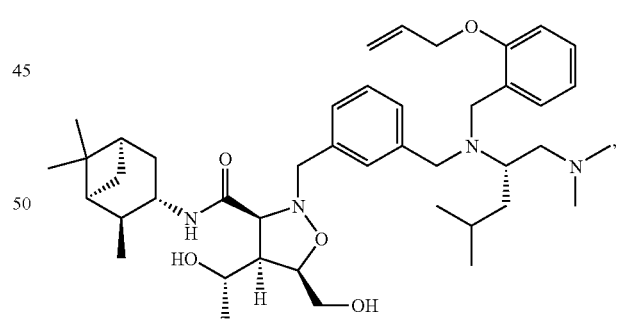

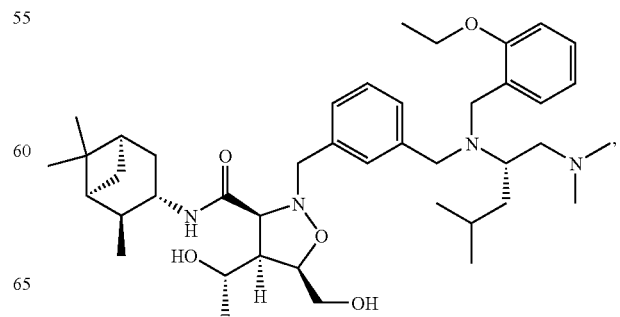

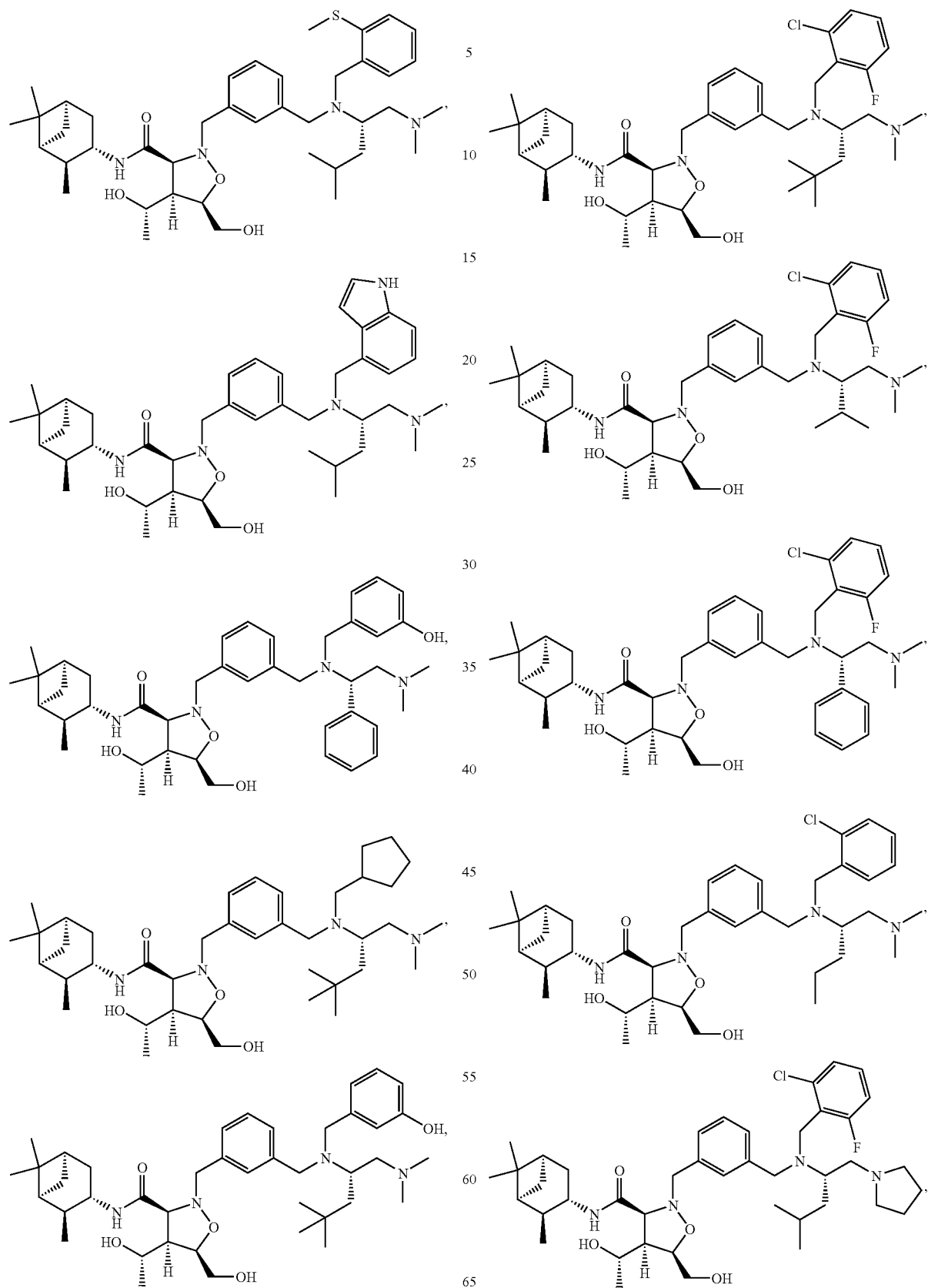

71
-continued
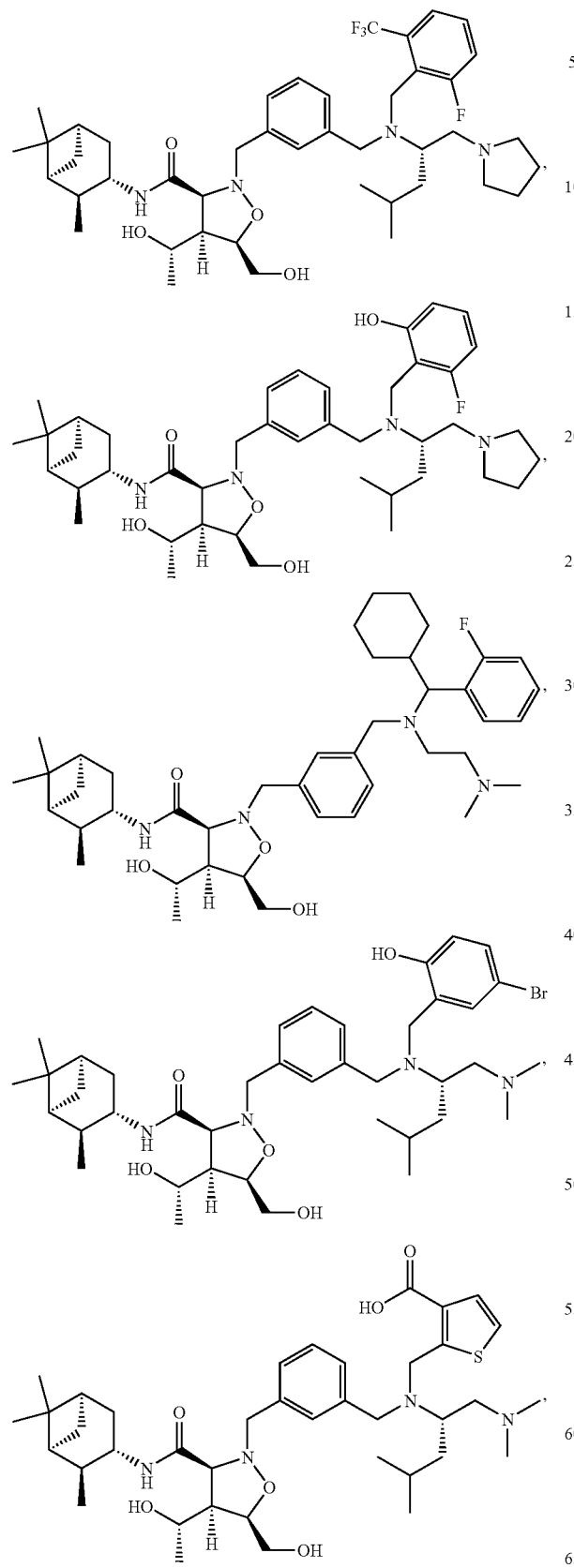
72
-continued
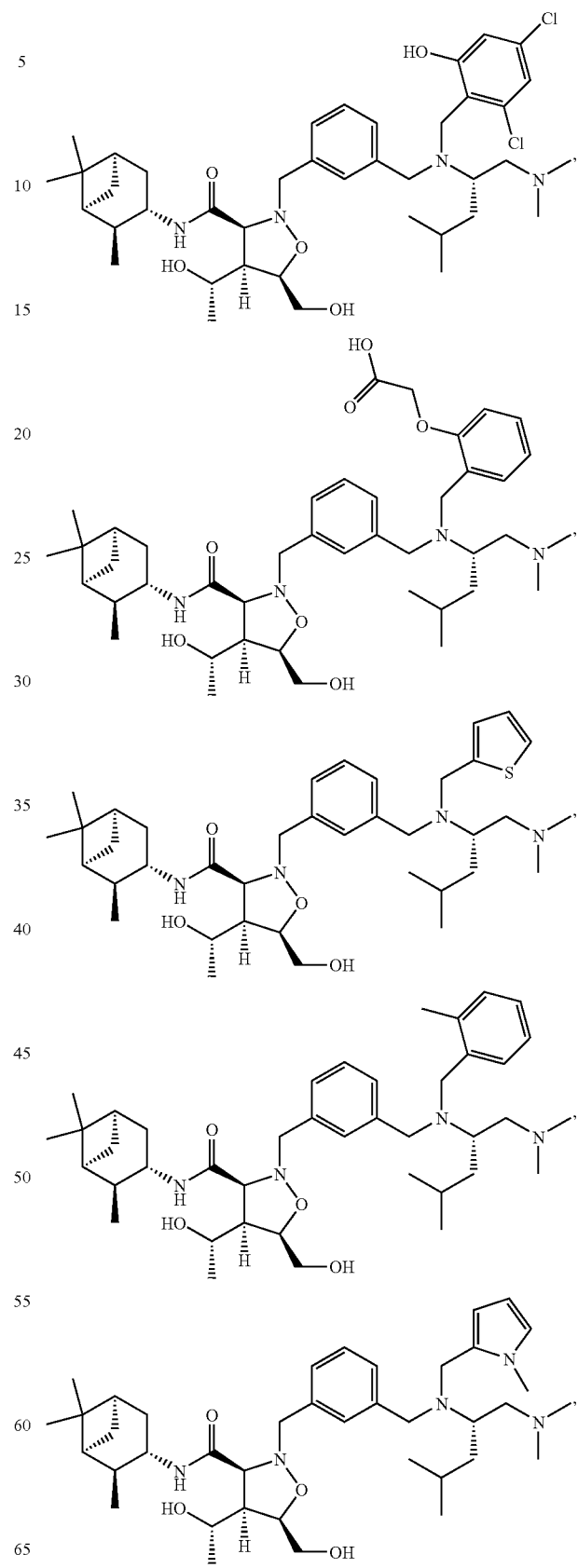

73
-continued
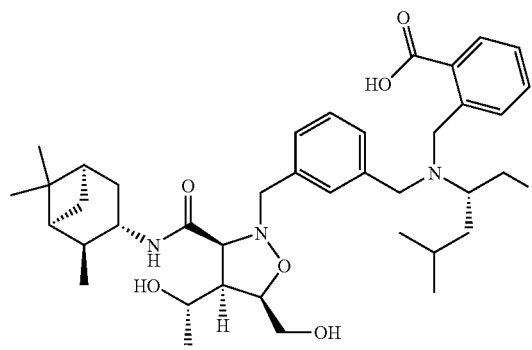
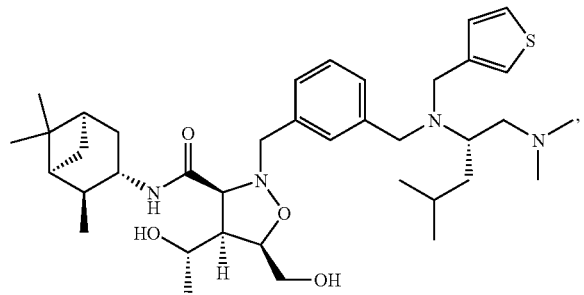
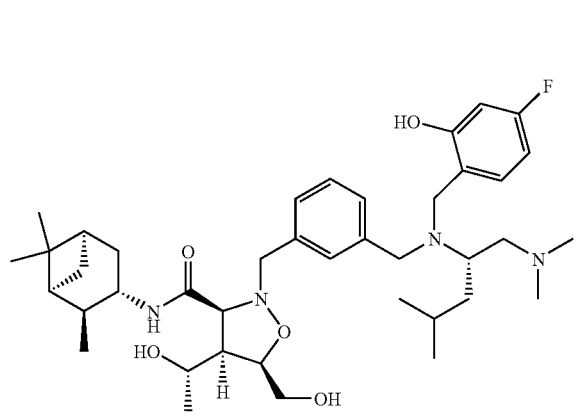
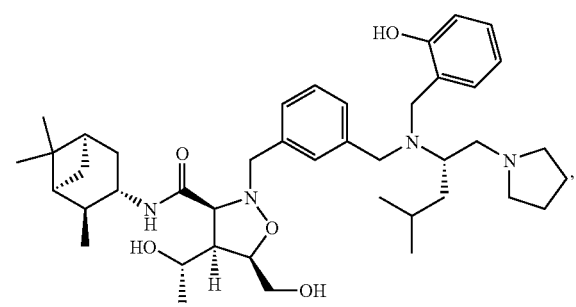
74
-continued
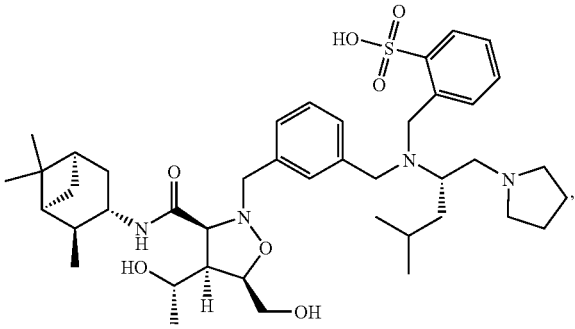
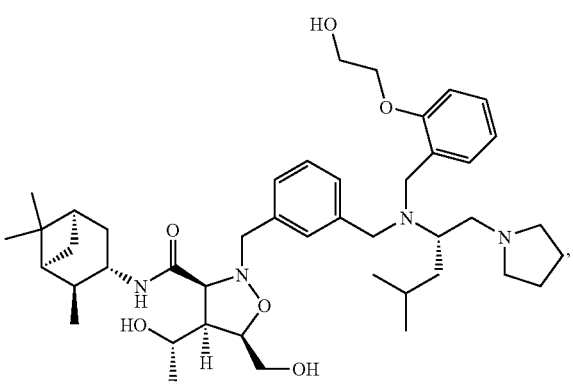
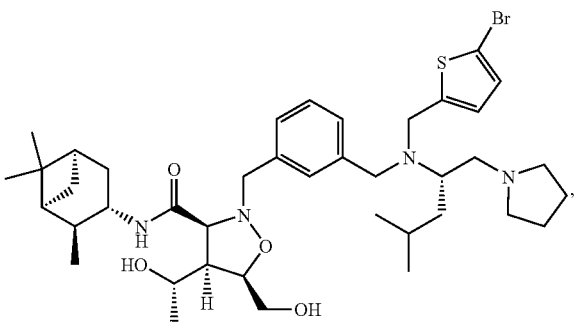
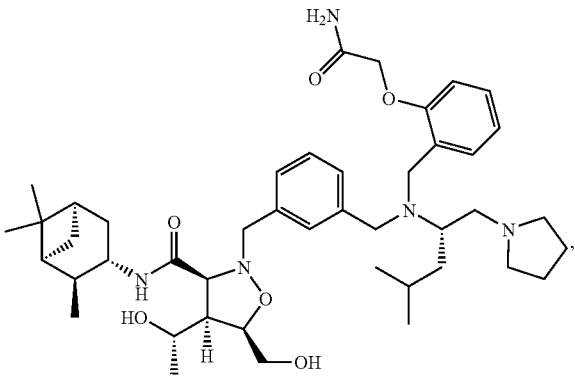

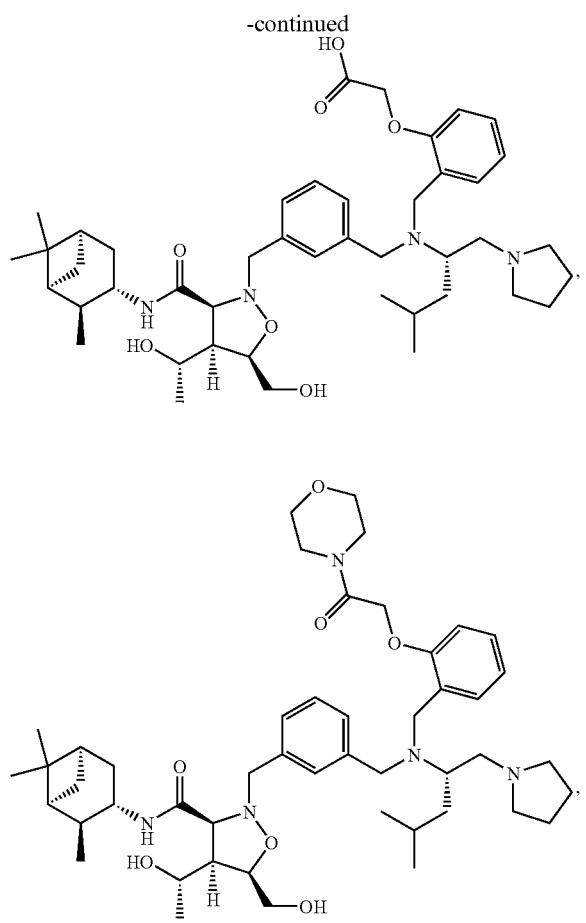
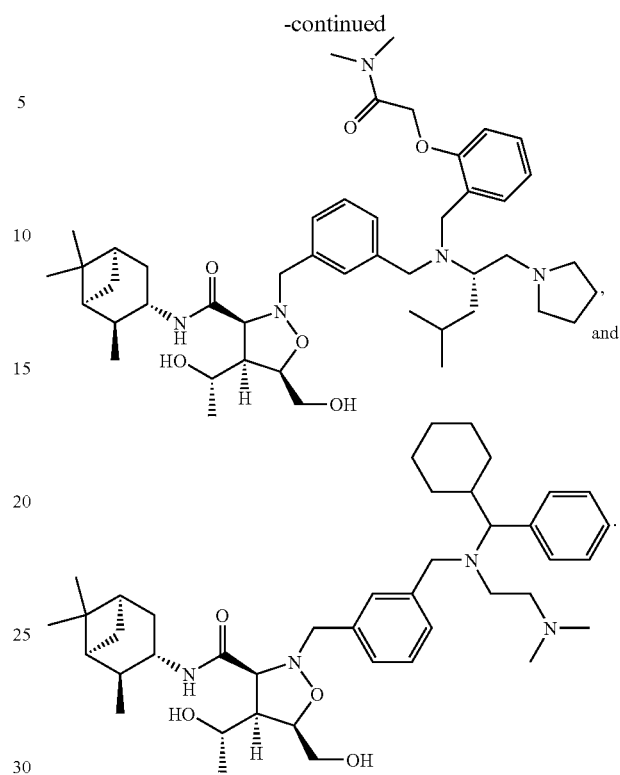
3. A pharmaceutical composition, comprising a compound of claim 1 or 2; and at least one pharmaceutically acceptable excipient.
* * * * *

UNITED STATES PATENT AND TRADEMARK OFFICE
CERTIFICATE OF CORRECTION

PATENT NO. : 7,842,815 B2
APPLICATION NO. : 11/600332
DATED : November 30, 2010
INVENTOR(S) : Castro et al.

Page 1 of 1

It is certified that error appears in the above-identified patent and that said Letters Patent is hereby corrected as shown below:

In column 17 at line 52, please replace:
"$-[C(R^5)(R^6)]_p-R^4$" with -- $-[C(R^5)(R^6)]_m-R^4$ --.

In claim 1, column 67 at lines 1-2, please replace:
"$-[C(R^5)(R^6)]_p-R^4$" with -- $-[C(R^5)(R^6)]_m-R^4$ --.

Signed and Sealed this
Twenty-seventh Day of September, 2011

David J. Kappos
*Director of the United States Patent and Trademark Office*